US007883850B2

(12) United States Patent
Song et al.

(10) Patent No.: US 7,883,850 B2
(45) Date of Patent: Feb. 8, 2011

(54) CRY1F AND CRY1AC TRANSGENIC COTTON LINES AND EVENT-SPECIFIC IDENTIFICATION THEREOF

(75) Inventors: Ping Song, Carmel, IN (US); Laura Ann Tagliani, Zionsville, IN (US); John William Pellow, Corcoran, CA (US)

(73) Assignee: Dow AgroSciences LLC, Indianapolis, IN (US)

( * ) Notice: Subject to any disclaimer, the term of this patent is extended or adjusted under 35 U.S.C. 154(b) by 725 days.

(21) Appl. No.: 11/704,418

(22) Filed: Feb. 9, 2007

(65) Prior Publication Data

US 2007/0143876 A1 Jun. 21, 2007

Related U.S. Application Data

(62) Division of application No. 10/964,838, filed on Oct. 13, 2004, now Pat. No. 7,179,965.

(60) Provisional application No. 60/556,586, filed on Mar. 26, 2004, provisional application No. 60/613,851, filed on Sep. 27, 2004.

(51) Int. Cl.
C12Q 1/68 (2006.01)
C12P 19/34 (2006.01)

(52) U.S. Cl. .......................... 435/6; 435/91.2; 536/23.1; 536/24.33

(58) Field of Classification Search .................. 435/6, 435/91.2; 536/23.1, 24.33
See application file for complete search history.

(56) References Cited

U.S. PATENT DOCUMENTS

| | | | |
|---|---|---|---|
| 5,188,960 A | 2/1993 | Payne et al. | |
| 5,571,937 A * | 11/1996 | Watanabe et al. | 560/147 |
| 5,691,308 A | 11/1997 | Payne et al. | |
| 5,710,020 A | 1/1998 | Adang | |
| 6,096,708 A | 8/2000 | Payne et al. | |
| 6,114,138 A | 9/2000 | Adang | |
| 6,162,965 A * | 12/2000 | Hansen | 800/278 |
| 6,218,188 B1 * | 4/2001 | Cardineau et al. | 435/468 |
| 6,229,004 B1 | 5/2001 | Adang | |
| 6,251,656 B1 | 6/2001 | Adang | |
| 6,573,240 B1 | 6/2003 | Payne et al. | |
| 2002/0120964 A1 | 8/2002 | Rangwala et al. | |
| 2003/0232410 A1 | 12/2003 | Liljedahl et al. | |
| 2004/0009504 A1 | 1/2004 | Rangwala et al. | |
| 2004/0123340 A1 * | 6/2004 | Deikman et al. | 800/278 |

FOREIGN PATENT DOCUMENTS

| WO | WO 98/22595 | 5/1998 |
|---|---|---|
| WO | WO 99/24581 | 5/1999 |
| WO | WO 01/13731 | 3/2001 |
| WO | WO 02/100163 | 12/2002 |
| WO | WO 03/080809 A2 | 10/2003 |
| WO | WO 2004/011601 | 2/2004 |
| WO | WO 2004/072235 | 8/2004 |

OTHER PUBLICATIONS

Lowe et al. Nucleic acid research, 1990, vol. 18(7), p. 1757-1761.*
The search reports.*
Adamczyk, J.J. Jr., "Laboratory and field performance of cotton containing Cry1ac, Cry1f, and both . . . ," Florida Entomologist (Dec. 2004), p. 427-432, vol. 87, No. 4.
Dow Agrosciences LLC, "Dow AgroSciences Receives Experimental Use Permit for Widestrike(™) Insect Protection," www.dowagro.com/usag/resource/20030423a.htm>, Apr. 23, 2005.
Dow Agrosciences LLC, "Agronomic assessment and seed increase of GM cotton expressing insecticidal genes . . . ", Application for License, DIR 040/2003 (Nov. 2003).
Perlak, F.J. et al., "Development and commercial use of Bollgard(R) cotton in the USA: Early promises," Plant Journal (Sep. 2001), p. 489-501, vol. 27, No. 6.

* cited by examiner

*Primary Examiner*—Kenneth R. Horlick
*Assistant Examiner*—Joyce Tung
(74) *Attorney, Agent, or Firm*—Donald R. Stuart; Baker & Daniels LLP

(57) ABSTRACT

This invention relates to plant breeding and the protection of plants from insects. More specifically, this invention includes novel transformation events of cotton plants comprising one or more polynucleotide sequences, as described herein, inserted into specific site(s) within the genome of a cotton cell. In highly preferred embodiments, said polynucleotide sequences encode "stacked" Cry1F and Cry1Ac lepidopteran insect inhibitory proteins. However, the subject invention includes plants having single cry1F or cry1Ac events, as described herein. Additionally, the invention is related to cotton plants derived from that transformation event and to assays for detecting the presence of the event in a sample. More specifically, the present invention provides DNA and related assays for detecting the presence of certain insect-resistance events in cotton. The assays are based on the DNA sequences of recombinant constructs inserted into the cotton genome and of the genomic sequences flanking the insertion sites. These sequences are unique. Based on these insert and border sequences, event-specific primers were generated. PCR analysis demonstrated that these cotton lines can be identified in different cotton genotypes by analysis of the PCR amplicons generated with these event-specific primer sets. Thus, these and other related procedures can be used to uniquely identify these cotton lines. Kits and conditions useful in conducting the assays are also provided. These materials and methods can also be used to assist breeding programs to further develop traits in cotton.

8 Claims, 1 Drawing Sheet

CRY1F AND CRY1AC TRANSGENIC COTTON LINES AND EVENT-SPECIFIC IDENTIFICATION THEREOF

CROSS-REFERENCE TO RELATED APPLICATIONS

This application is a divisional of U.S. Ser. No. 10/964,838, filed Oct. 13, 2004, now U.S. Pat. No. 7,179,965 which claims the benefit of provisional application Ser. No. 60/556,586, filed Mar. 26, 2004, and to provisional application Ser. No. 60/613,851, filed Sep. 27, 2004.

BACKGROUND OF THE INVENTION

Cotton is an important fiber crop. Breeding and biotechnology have been applied to cotton to improve its agronomic traits and the quality of the product. One such agronomic trait is resistance to insects, the advantages of which are readily apparent. Genes encoding insecticidal proteins have been introduced into cotton plants. In order to alleviate any concern that a given type of insect could develop resistance to a single type of insecticidal protein, plants are often developed that produce two different types of insecticidal proteins. Thus, the odds of an insect being hypothetically capable of developing resistance to two different insecticidal proteins are extremely low.

Cry1Ac insecticidal proteins and genes are known in the art. See, e.g., U.S. Pat. Nos. 6,114,138; 5,710,020; 6,251,656; and 6,229,004. Cry1F insecticidal proteins and genes are also known in the art. See, e.g., U.S. Pat. Nos. 5,188,960; 5,691,308; 6,096,708; and 6,573,240.

The expression of foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., *Ann. Rev. Genet* 22:421-477, 1988). For example, the same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, it is necessary to create and screen a large number of events in order to identify an event that optimally expresses an introduced gene of interest. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method such as polymerase chain reaction (PCR) or DNA hybridization using nucleic acid probes. These detection methods generally focus on frequently used genetic elements, such as promoters, terminators, marker genes, and the like. As a result, such methods may not be useful for discriminating between different events, particularly those produced using the same DNA construct, unless the sequence of chromosomal DNA adjacent to the inserted DNA ("flanking DNA") is known. An event-specific PCR assay is discussed, for example, by Windels et al. (Med. Fac. Landbouww, Univ. Gent 64/5b:459462, 1999). This related to the identification of glyphosate tolerant soybean event 40-3-2 by PCR using a primer set spanning the junction between the insert and flanking DNA. More specifically, one primer included sequence from the insert and a second primer included sequence from flanking DNA.

U.S. Patent Apps. 20020120964 A1 and 20040009504 A1 relate to cotton event PV-GHGT07(1445) and compositions and methods for the detection thereof. WO 02/100163 relates to cotton event MON15985 and compositions and methods for the detection thereof. WO 2004/011601 relates to corn event MON863 plants and compositions and methods for the detection thereof. WO 2004/072235 relates to cotton event MON 88913 and compositions and methods for the detection thereof.

However, no such procedures and materials were specifically known, heretofore, that could be used to specifically identify Cry1F and/or Cry1Ac stacked cotton as discussed below.

BRIEF SUMMARY OF THE INVENTION

This invention relates to plant breeding and the protection of plants from insects. More specifically, this invention includes novel transformation events of cotton plants comprising one or more polynucleotide sequences, as described herein, inserted into specific site(s) within the genome of a cotton cell. In highly preferred embodiments, said polynucleotide sequences encode "stacked" Cry1F and Cry1Ac lepidopteran insect inhibitory proteins. However, the subject invention includes plants having single Cry1F or Cry1Ac events, as described herein.

Additionally, the subject invention provides assays for detecting the presence of one or more of the subject events in a sample. The present invention provides DNA and related assays for detecting the presence of certain insect-resistance events in cotton. The assays are based on the DNA sequences of recombinant constructs inserted into the cotton genome and of the genomic sequences flanking the insertion sites. Kits and conditions useful in conducting the assays are also provided.

Thus, the subject invention relates in part to the cloning and analysis of the DNA sequences of a whole cry1F insert, whole cry1Ac inserts, and the border regions thereof (in transgenic cotton lines). These sequences are unique. Based on these insert and border sequences, event-specific primers were generated. PCR analysis demonstrated that these events can be identified by analysis of the PCR amplicons generated with these event-specific primer sets. Thus, these and other related procedures can be used to uniquely identify cotton lines comprising one or more events of the subject invention.

BRIEF DESCRIPTION OF THE SEQUENCES

Figure 1:
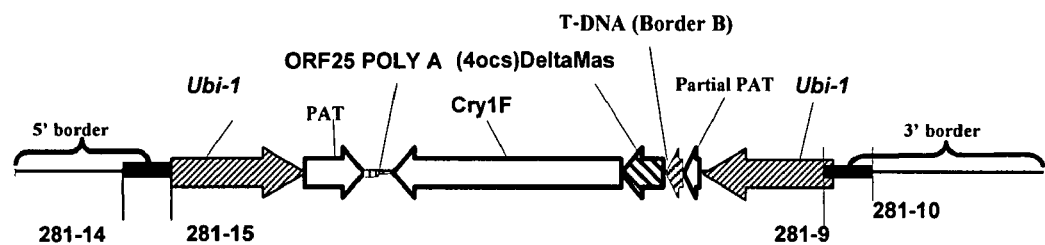
FIG. 1 illustrates the inserted cry1F transgene and flanking sequences for cotton event 281-24-236. This Figure also shows amplicons and primers as described herein.

SEQ ID NO:1 is the DNA sequence for the cry1F event 281-24-236 insert and its border sequences.

SEQ ID NO:2 is the DNA sequence for the cry1Ac event 3006-210-23 insert and its border sequences.

SEQ ID NO:3 is the sequence of forward primer "281-14" used with reverse primer "281-15" to amplify a 603 bp amplicon that spans the 5' junction between the flanking and insert regions of cry1F event 281-24-236.

SEQ ID NO:4 is the sequence of the reverse primer "281-15" used with forward primer "281-14" to amplify a 603 bp amplicon that spans the 5' junction between the flanking and insert regions of cry1F event 281-24-236.

SEQ ID NO:5 is the 603 bp sequence of the amplicon produced using the primers of SEQ ID NOS:3 and 4.

SEQ ID NO:6 is the sequence of forward primer "281-9" used with reverse primer "281-10" to amplify a 562 bp amplicon that spans the 3' junction between the insert and flanking regions of cry1F event 281-24-236.

SEQ ID NO:7 is the sequence of the reverse primer "281-10" used with forward primer "281-9" to amplify a 562 bp amplicon that spans the 3' junction between the flanking and insert regions of cry1F event 281-24-236.

SEQ ID NO:8 is the 562 bp sequence of the amplicon produced using the primers of SEQ ID NOS:6 and 7.

SEQ ID NO:9 is the sequence of forward primer "3006-20" used with reverse primer "3006-22" to amplify a 614 bp amplicon that spans the 5' junction between the flanking and insert regions of cry1Ac event 3006-210-23.

SEQ ID NO:10 is the sequence of the reverse primer "3006-22" used with forward primer "3006-20" to amplify a 614 bp amplicon that spans the 5' junction between the flanking and insert regions of cry1Ac event 3006-210-23.

SEQ ID NO:11 is the 614 bp sequence of the amplicon produced using the primers of SEQ ID NOS:9 and 10.

SEQ ID NO:12 is the sequence of forward primer "3006-9" used with reverse primer "3006-12" to amplify a 662 bp amplicon that spans the 3' junction between the insert and flanking regions of cry1Ac event 3006-210-23.

SEQ ID NO:13 is the sequence of the reverse primer "3006-12" used with forward primer "3006-9" to amplify a 662 bp amplicon that spans the 3' junction between the flanking and insert regions of cry1Ac event 3006-210-23.

SEQ ID NO:14 is the 662 bp sequence of the amplicon produced using the primers of SEQ ID NOS:12 and 13.

SEQ ID NO:15 is a segment of genomic cotton DNA for event 281-24-236 (53 missing bases).

SEQ ID NO:16 is a segment of genomic cotton DNA for event 3006-210-23 (16 missing bases).

DETAILED DESCRIPTION OF THE INVENTION

This invention relates to plant breeding and the protection of plants from insects. More specifically, this invention includes novel transformation events of cotton plants (e.g. *Gossypium hirsutum* and *Gossypium barbadense*) comprising one or more polynucleotide sequences, as described herein, inserted into specific site(s) within the genome of a cotton cell. In highly preferred embodiments, said polynucleotide sequences encode "stacked" Cry1F and Cry1Ac lepidopteran insect inhibitory proteins. However, the subject invention includes plants having single Cry1F or Cry1Ac events, as described herein.

Additionally, the subject invention provides assays for detecting the presence of one or more of the subject events in a sample. Aspects of the subject invention include methods of designing and/or producing any of the diagnostic nucleic acid molecules exemplified or suggested herein, particularly those based wholly or partially on the subject flanking sequences.

More specifically, the subject invention relates in part to two transgenic cotton events (cry1F 281-24-236 and cry1Ac 3006-210-23), plant lines comprising these events, and the cloning and analysis of the DNA sequences of this cry1F insert, these cry1Ac inserts, and/or the border regions thereof. Plant lines of the subject invention can be detected using sequences disclosed and suggested herein.

In preferred embodiments, this invention relates to insect-resistant cotton lines, and the identification thereof, that produces two "stacked" insecticidal proteins known as Cry1F and Cry1Ac. In preferred embodiments, a plant line of the subject invention comprises Cry1F event 281-24-236 and cry1Ac event 3006-210-23. However, plants of the subject invention can comprise any one or, preferably, both of the events discussed herein.

As alluded to above in the Background section, the introduction and integration of a transgene into a plant genome involves some random events (hence the name "event" for a given insertion that is expressed). That is, with many transformation techniques such as *Agrobacterium* transformation, the "gene gun," and WHISKERS, it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

As "events" are random events and generally cannot be duplicated, as part of this disclosure at least 2500 seeds of a cotton line, comprising the cry1F event 281-24-236 and cry1Ac event 3006-210-23, have been deposited, and made available to the public without restriction (but subject to patent rights), with the American Type Culture Collection (ATCC), Rockville, Md. 20852. The deposit has been designated as ATCC Deposit No. PTA-6233. The deposit will be maintained without restriction at the ATCC depository, which is a public depository, for a period of 30 years, or five years after the most recent request, or for the effective life of the patent, whichever is longer, and will be replaced if it becomes nonviable during that period.

The deposited seeds are part of the subject invention. Clearly, cotton plants can be grown from these seeds, and such plants are part of the subject invention. The subject invention also relates to DNA sequences contained in these cotton plants that are useful for detecting these plants and progeny thereof. Detection methods and kits of the subject invention can be directed to identifying any one, two, or even all three of these events, depending on the ultimate purpose of the test.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the cotton native genome flanking the insertion point, the identification or detection of one or the other junction sequences in a plant's genetic material being sufficient to be diagnostic for the event. Included are the DNA sequences that span the insertions in herein-described cotton events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates to the identification of such flanking, junction, and insert sequences. Related PCR primers and amplicons are included in the invention. According to the subject invention, PCR analysis methods using amplicons that span across inserted DNA and its borders (of Cry1F 281-24-236 and/or Cry1Ac 3006-210-23) can be used to detect or identify commercialized transgenic cotton varieties or lines derived from the subject proprietary transgenic cotton lines.

The entire sequences of each of these inserts, together with the respective flanking sequences, are provided herein as SEQ ID NO:1 (cry1F 281-24-236) and SEQ ID NO:2 (cry1Ac 3006-210-23). Table 1 provides the coordinates of the insert and flanking sequences for these events.

TABLE 1

| Event | For indicated SEQ ID NO:, residue location of: | | |
|---|---|---|---|
| | 5' Flanking | Insert | 3' Flanking |
| cry1F 281-24-236 (SEQ ID NO: 1) | 1-2074 | 2,075-12,748 | 12,749-15,490 |
| cry1Ac 3006-210-23 (SEQ ID NO: 2) | 1-527 | 528-8,900 | 8,901-9,382 |

Figure 2:
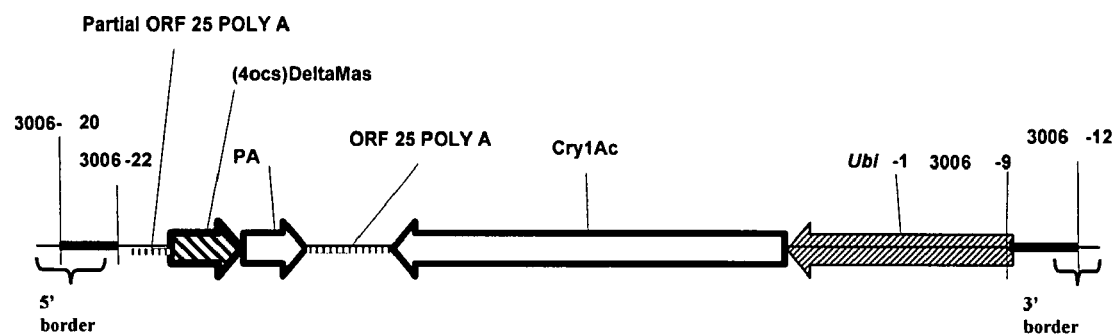
FIG. 2 illustrates an inserted cry1Ac transgene and flanking sequences for cotton event 3006-210-23. This Figure also shows amplicons and primers as described herein.

These insertion events, and further components thereof, are further illustrated in FIGS. 1 and 2. These sequences (particularly the flanking sequences) are unique. Based on these insert and border sequences, event-specific primers were generated. PCR analysis demonstrated that these cotton lines can be identified in different cotton genotypes by analysis of the PCR amplicons generated with these event-specific primer sets. Thus, these and other related procedures can be used to uniquely identify these cotton lines. The sequences identified herein are unique. For example, BLAST searches against GENBANK databases did not reveal any significant homology between the cloned border sequences and sequences in the database.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit cotton breeding programs as well as quality control, especially for commercialized transgenic cottonseeds. PCR detection kits for these transgenic cotton lines can also now be made and used. This can also benefit product registration and product stewardship.

Furthermore, flanking cotton sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that the subject invention includes seeds available under ATCC Deposit No. PTA-6233. The subject invention also includes an insect-resistant cotton plant grown from a seed deposited with the ATCC under accession number PTA-6233. The subject invention further includes parts of said plant, such as leaves, tissue samples, seeds produced by said plant, pollen, and the like.

Still further, the subject invention includes descendant and/or progeny plants of plants grown from the deposited seed, preferably an insect-resistant cotton plant wherein said plant has a genome comprising a detectable wild-type genomic DNA/insert DNA junction sequence as described herein. As used herein, the term "cotton" means *Gossypium hirsutum* and includes all plant varieties that can be bred with cotton, including *Gossypium barbadense*.

This invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

An insect-resistant cotton plant can be bred by first sexually crossing a first parental cotton plant consisting of a cotton plant grown from seed of any one of the lines referred to herein, and a second parental cotton plant, thereby producing a plurality of first progeny plants; and then selecting a first progeny plant that is resistant to insects (or that possesses at least one of the events of the subject invention); and selfing the first progeny plant, thereby producing a plurality of second progeny plants; and then selecting from the second progeny plants a plant that is resistant to insects (or that possesses at least one of the events of the subject invention). These steps can further include the back-crossing of the first progeny plant or the second progeny plant to the second parental cotton plant or a third parental cotton plant. A cotton crop comprising cotton seeds of the subject invention, or progeny thereof, can then be planted.

It is also to be understood that two different transgenic plants can also be mated to produce offspring that contain two independently segregating added, exogenous genes. Selfing of appropriate progeny can produce plants that are homologous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homologous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting parent is expected to have the attributes of the recurrent parent (e.g., cultivar) and the desirable trait transferred from the donor parent.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The insect-resistance trait can be tracked in the progeny of a cross with a cotton plant of the subject invention (or progeny thereof and any other cotton cultivar or variety) using the MAB methods. The DNA molecules are markers for this trait, and MAB methods that are well known in the art can be used to track the insect-resistance trait(s) in cotton plants where at least one cotton line of the subject invention, or progeny thereof, was a parent or ancestor. The methods of the present invention can be used to identify any cotton variety having the insect-resistance event from cotton line 281-24-236 (cry1F) and/or 3006-210-23 (cry1Ac).

Methods of the subject invention include a method of producing an insect-resistant cotton plant wherein said method comprises breeding with a plant of the subject invention. More specifically, said methods can comprise crossing two plants of the subject invention, or one plant of the subject invention and any other plant. Preferred methods further comprise selecting progeny of said cross by analyzing said progeny for an event detectable according to the subject invention.

A preferred plant, or a seed, of the subject invention comprises in its genome at least one of the insert sequences, as identified in Table 1, together with at least 20-500 or more contiguous flanking nucleotides on both sides of the insert, as identified in Table 1. Unless indicated otherwise, "cry1F cotton event 281-24-236" refers to DNA of SEQ ID NO:1 that includes the heterologous DNA inserted in the original transformant (nucleotides 2075-12,748 of SEQ ID NO:1) and all or part of both of the flanking genomic sequences of SEQ ID NO:1 (nucleotide residues 1-2074 and 12,749-15,490) immediately adjacent to the inserted DNA that would be expected to be transferred to progeny that receives the inserted DNA as a result of a sexual cross of a parental line that includes the event. Similarly, unless indicated otherwise, "cry1xAc cotton event 3006-210-23" refers to DNA of SEQ ID NO:2 that includes the heterologous DNA inserted in the original transformant (nucleotides 528-8900 of SEQ ID NO:2) and all or part of both of the flanking genomic sequences of SEQ ID NO:2 (residues 1-527 and 8901-9382) immediately adjacent to the inserted DNA that would be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when (i) it is predominantly derived from the initial variety, or from a variety that is itself predominantly derived from the initial variety, while retaining the expression of the essential characteristics that result from the genotype or combination of genotypes of the initial variety;

(ii) it is clearly distinguishable from the initial variety; and (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial canola variety without the premium value traits grown in the same region.

"Agronomically elite" means that a line has desirable agronomic characteristics such as yield, maturity, disease resistance, and the like, in addition to the insect resistance due to the subject event(s).

As one skilled in the art will recognize in light of this disclosure, preferred embodiments of detection kits, for example, can include probes and/or primers directed to and/or comprising "junction sequences" or "transition sequences" (where the cotton genomic flanking sequence meets the insert sequence). For example, this includes a polynucleotide probe, primer, or amplicon comprising a sequence including residues 2074-2075 or 12,748-12,749 of SEQ ID NO:1, or residues 527-528 or 8,900-8,901 of SEQ ID NO:2, as indicated in Table 1. To be diagnostic for these particular events, preferred "junction primers" should include at least ~15 residues of the adjacent flanking sequence and at least ~15 residues of the adjacent insert sequence. With this arrangement, another primer in either the flanking or insert region can be used to generate a detectable amplicon that indicates the presence of an event of the subject invention. In preferred embodiments, however, one primer binds in the flanking region and one binds in the insert, and these primers can be used to generate an amplicon that spans (and includes) a junction sequence as indicated above.

One skilled in the art will also recognize that primers and probes can be designed to hybridize, under a range of standard hybridization and/or PCR conditions, to a segment of SEQ ID NO:1, SEQ ID NO:2, and complements thereof, wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be further noted that errors in PCR amplification can occur which might result in minor sequencing errors, for example. That is, unless otherwise indicated, the sequences listed herein were determined by generating long amplicons from cotton genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. For example, the following differences between the determined sequences of the event-flanking DNAs and the corresponding, known/wild-type/genomic DNAs are noted. In the 5' flank for the subject cry1F event, residue 2037 of SEQ ID NO:1 was determined to be/is listed as "G" whereas the corresponding residue of the 281-24-236 locus of the known genomic sequence is "A" (R can be used in a consensus sequence, according to standard IUPAC-IUB conventions). In the 3' flank of this event, residue 12,781 of SEQ ID NO:1 is listed herein as T whereas C is provided in the published genomic sequence at the corresponding location (Y is the consensus code). Position 12,811 of SEQ ID NO:1 is C whereas T is provided for the genome (Y would be the consensus). Position 12,866 is listed as C in SEQ ID NO:1 whereas T appears in the genome (Y is the consensus). Position 12,882 is listed as G in SEQ ID NO:1 whereas A appears for the genome (R is the consensus). Position 12,918 is listed as A in SEQ ID NO:1 wheres G appears in the genome (R is the consensus). Residue 13,129 is listed as G in SEQ ID NO:1 whereas A appears in the genome (R is the consensus). Residue 13,222 is listed as C in SEQ ID NO:1 whereas T appears in the genomic sequence (Y is the consensus). At position 13,441 in SEQ ID NO:1, a T appears whereas there is no corresponding residue in the genomic listing. Thus, this apparent insertion would shift the downstream numbering of SEQ ID NO:1 accordingly, as compared to the genomic sequence. One skilled in the art should recognize and be put on notice than any adjustments needed due to these types of common sequencing errors or discrepancies are within the scope of the subject invention.

Similar differences also appear in the 5' flank for the subject cry1Ac event. At positions 149, 153, 159, 165, and 244 of SEQ ID NO:2, the following residues are listed, respectively: C, G, C, C, and C. In the genomic sequence at the 3006-210-23 locus, the following residues appear, respectively, at corresponding locations: A, A, A, A, and A. Consensus codes for these substitutions are, respectively, M, R, M, M, and M. Adjustments to probes and primers can be made accordingly, and corresponding differences might be noted in amplicons that span or include any of the above residues.

It should also be noted that it is not uncommon for some genomic sequence to be deleted when a sequence is inserted during the creation of an event. This was the case for both events of the subject invention. That is, SEQ ID NO:1 provides a 53-base segment of genomic cotton DNA for event 281-24-236 that was deleted during the insertion. This "interior segment" occurs between residues 2074 and 12,749 of SEQ ID NO:1 in the non-transformed cotton genome. Similarly, SEQ ID NO:2 provides a 16-base segment of genomic cotton DNA for event 3006-210-23 that was deleted during the insertion. This "interior segment" occurs between residues 527 and 8,901 of SEQ ID NO:2 in the non-transformed cotton genome.

As illustrated in FIGS. 1 and 2, the components of each of the "inserts" are as follows. The transgene genetic element DNA molecules contained in the subject event Cry1F 281-24-236 consists of the maize ubiquitin 1 promoter, operably connected to the phosphinothricin N-acetyltransferase (PAT) from *Streptomyces viridochromogenes*, operably connected to the ORF25 polyadenylation sequences (Baker et al., *Plant Molecular Biology* 2:335-350, 1983); the chimeric promoter [(4OCS)δMAS] containing a partially deleted mannopines synthase promoter with 4 enhancer elements from the octopine synthase promoter, operably connected to the Cry1F (synpro) from *Bacillus thuringiensis* var. aizawai, operably connected to ORF25 polyadenylation sequences (Baker et al., *Plant Molecular Biology* 2:335-350, 1983); and the maize ubiquitin 1 promoter unoperably connected to a partial pat sequence. The DNA polynucleotide sequences or fragments of these components can be used as DNA primers or probes in the methods of the present invention.

The transgene genetic element DNA molecules contained in the subject event Cry1Ac 3006-210-23 consists of the (4OCS)6MAS promoter operably connected to the PAT (as described above), operably connected to the ORF25; and the maize ubiquitin 1 promoter operably connected to the Cry1Ac (synpro) from *Bacillus thuringiensis* var. kurstaki, operably connected to the the ORF25 polyadenylation sequences. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a cotton plant designated WIDESTRIKE comprising Cry1F event 281-24-236 and Cry1Ac event 3006-210-23. DNA sequences are provided that comprise at least one transgene/genomic insertion region junction sequence provided herein in SEQ ID NO:1, SEQ ID NO:2, segments thereof, and complements of the exemplified sequences and any segments thereof. The insertion region junction sequence spans the junction between heterologous DNA inserted into the genome and the DNA from the cotton cell flanking the insertion site. Such sequences are diagnostic for one or more of the given events.

Based on these insert and border sequences, event-specific primers were generated. PCR analysis demonstrated that these cotton lines (Cry1F 281-24-236 and Cry1Ac 3006-210-23) can be identified in different cotton genotypes by analysis of the PCR amplicons generated with these event-specific primer sets. These and other related procedures can be used to uniquely identify these cotton lines. Thus, PCR amplicons derived from such primer pairs are unique and can be used to identify these cotton lines.

In some embodiments, DNA sequences that comprise at least one of the novel transgene/genomic insertion regions are an aspect of this invention. Included are DNA sequences that comprise a sufficient length of polynucleotides of transgene insert sequence and a sufficient length of polynucleotides of cotton genomic sequence from one or more of the three aforementioned cotton plants and/or sequences that are useful as primer sequences for the production of an amplicon product diagnostic for one or more of these cotton plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence selected from the group consisting of SEQ ID NO:1 and SEQ ID NO:2, or complements thereof, and a similar length of flanking cotton DNA sequence from these sequences, or complements thereof. Such sequences are useful as DNA primers in DNA amplification methods. The amplicons produced using these primers are diagnostic for any of the cotton events referred to herein. Therefore, the invention also includes the amplicons produced by such DNA primers and homologous primers.

Following is a table that summarizes specific embodiments of the subject invention:

This invention also includes methods of detecting the presence of DNA, in a sample, that corresponds to at least one of the cotton events referred to herein. Such methods can comprise: (a) contacting the sample comprising DNA with a primer set that, when used in a nucleic acid amplification reaction with DNA from at least one of these cotton events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to at least one of said events, wherein said method comprises: (a) contacting the sample comprising DNA with a probe that hybridizes under stringent hybridization conditions with DNA from at least one of said cotton events and which does not hybridize under the stringent hybridization conditions with a control cotton plant (non-event-of-interest DNA); (b) subjecting the sample and probe to stringent hybridization conditions; and (c) detecting hybridization of the probe to the DNA.

In still further embodiments, the subject invention includes methods of producing a cotton plant comprising a cry1F and/or a cry1Ac event of the subject invention, wherein said method comprises the steps of: (a) sexually crossing a first parental cotton line (comprising an expression cassettes of the present invention, which confers said insect resistance trait to plants of said line) and a second parental cotton line (that lacks this insect tolerance trait) thereby producing a plurality of progeny plants; and (b) selecting a progeny plant by the use of molecular markers. Such methods may optionally comprise the further step of back-crossing the progeny plant to the second parental cotton line to producing a true-breeding cotton plant that comprises said insect tolerance trait.

According to another aspect of the invention, methods of determining the zygosity of progeny of a cross with any one (or more) of said three events are provided. Said methods can comprise contacting a sample, comprising cotton DNA, with a primer set of the subject invention. Said primers, when used in a nucleic-acid amplification reaction with genomic DNA from at least one of said cotton events, produce a first amplicon that is diagnostic for at least one of said cotton events.

TABLE 2

List of Primers and Their Sequences Used in Event-Specific PCR Amplification

| Event | Forward Sequence (5'-3) | Reverse Sequence (5'-3') | Amplicon Size (bp) | Target Region |
|---|---|---|---|---|
| 281-24-236 | tgtcggctgaaggtagggagg (281-14) (SEQ ID NO: 3) | ccggacatgaagccatttac (281-15) (SEQ ID NO: 4) | 603 (SEQ ID NO: 5) | 5' insert junction |
|  | tctctagagaggggcacgacc (281-9) (SEQ ID NO: 6) | Cgagctggagagaccggtgac (281-10) (SEQ ID NO: 7) | 562 (SEQ ID NO: 8) | 3' insert junction |
| 3006-210-23 | ttccaacctttaactattatcctgc (3006-20) (SEQ ID NO: 9) | gctgcggacatctacatttt (3006-22) (SEQ ID NO: 10) | 614 (SEQ ID NO: 11) | 5' insert junction |
|  | gacatgcaatgctcattatctcta (3006-9) (SEQ ID NO: 12) | Aagtctctgccttctaccctgg (3006-12) (SEQ ID NO: 13) | 662 (SEQ ID NO: 14) | 3' insert junction |

Such methods further comprise performing a nucleic acid amplification reaction, thereby producing the first amplicon; detecting the first amplicon; and contacting the sample comprising cotton DNA with said primer set (said primer set, when used in a nucleic-acid amplification reaction with genomic DNA from cotton plants, produces a second amplicon comprising the native cotton genomic DNA homologous to the cotton genomic region of a transgene insertion identified as one of said cotton events); and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject cotton event DNA in a sample and can be applied to methods for breeding cotton plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said cotton events, whether from a cotton plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is fuinctionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence set forth in SEQ ID NOS:3-14, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequences. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of the present invention, DNA extracted from a cotton plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject cotton event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed two general locations in the cotton genome that are excellent for insertions, the subject invention also comprises a cotton seed and/or a cotton plant comprising at least one non-cry1F and non-cry1Ac insert in the general vicinity of one or both of these locations. One option is to substitute a different insert in place of the cry1F and/or cry1Ac insert exemplified herein. In these generally regards, targeted homologous recombination, for example, can be used according to the subject invention. This type of technology is the subject of, for example, WO 03/080809 A2 and the corresponding published U.S. application (USPA 20030232410).

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention.

Unless otherwise indicated, all percentages are by weight and all solvent mixture proportions are by volume unless otherwise noted.

Example 1

Production of Deposited Seed

WideStrike™ brand insect resistance for cotton is a transgenic trait developed by Dow AgroSciences that provides in-plant insect resistance against Lepidoptera. It contains two insect tolerance genes, cry1Ac and cry1F, which were derived from *Bacillus thuringiensis* subspecies *kurstaki* and *Bacillus thuringiensis* subspecies *aizawai*, respectively. *Bacillus thuringiensis* (B.t.) is a common, gram-positive, soil-borne bacterium. In its spore-forming stage, it produces several insecticidal protein crystals (known as delta-endotoxins) including Cry1Ac and Cry1F. These proteins are toxic to certain lepidopteran insects. In susceptible insects, they bind to specific receptors present on midgut epithelial cells, forming pores that disrupt osmotic balance and eventually result in cell lysis and death. Cry1Ac and Cry1F have been shown to be nontoxic to humans, livestock, and beneficial insects, which do not have binding sites for the delta-endotoxin. Using two delta-endotoxins rather than one will provide improved insect resistance because the two Cry proteins provide a greater spectrum of control than either does alone and have differential activity against the lepidopteran pests that they are effective against. More importantly, it may help delay the development of resistant insects.

The cry1Ac and cry1F genes in WideStrike were introduced using *Agrobacterium* mediated transformation into GC-510 cotton (*Gossypium hirsutum* L.) plants in two separate transformation events, 3006-210-23 and 281-24-236. Following crossing into an elite cotton variety, these events were combined by conventional breeding to produce cotton bearing the WideStrike insect-resistance trait. WideStrike also contains the pat gene from *Streptomyces viridochromogenes*, a common aerobic soil bacteria. The pat gene codes for the Phosphinothricin Acetyl Transferase (PAT) enzyme, which detoxifies glufosinate ammonium into an inactive compound by acetylation. The pat gene was included to allow for selection of transformed cotton plants.

Example 2

Diagnostic Test for Cry1F Cotton Event 281-24-236

DNA from Cry1F event 281-24-236 and Cry1Ac events 3006-210-23, and non-transgenic cotton PCS355 was extracted from cotton leaves using QIAGEN's Plant DNeasy kit (catalog #69181, Qiagen, Valencia, Calif., USA). The manufacturer's suggested protocol was followed. In brief, leaf discs were disrupted in an RNAse supplemented preheated buffer using a tungsten carbide bead (0.125 mm diameter) and a Retsch MM3000 Mixer Mill. The mixture was centrifuged at room temperature, and the supernatant was subsequently captured by running through a DNeasy 96 plate. DNA was eluted in an elution buffer and stored frozen until use.

The DNA extracted from the cotton leaf tissue was used in a PCR DNA amplification of the 5' genomic/transgene insert sequences in Cry1F event 281-24-236 using primer 281-14 (SEQ ID NO:3, 5'TGTCGGCTGAAGGTAGGGAGG3') and primer 281-15 (SEQ ID NO:4, 5'CCGGACATGAAGCCATTTAC3'), and the 3' genomic/transgene insert sequences flanking using primer 281-9 (SEQ ID NO:6, 5'TCTCTAGAGAGGGGCACGACC3') and primer 281-10 (SEQ ID NO:7, 5'CGAGCTGGAGAGACCGGTGAC3'). The PCR DNA amplification analyses were conducted using genomic DNA extracted from cotton event Cry1F 281-24-236 and non-transgenic cotton line PCS355. The amplification reaction for the 5' flanking genomic sequence was conducted using QIAGEN HotStarTaq PCR kit (catalog #203203 or 203205, QIAGEN, Valencia, Calif., USA) with a final concentration of 0.4 µM for Primer 281-14 and Primer 281-15 in a 50 µl reaction volume. The reactions were performed using a GenAmp PCR System 9600 (Applied Biosystem, Foster City, Calif.) under the following cycling conditions: 1 cycle at 95° C. for 15 minute; 35 cycles of 94° C. for 30 seconds, 57° C. for 30 seconds, 72° C. for 60 seconds; 1 cycle at 72° C. for 10 minutes. The PCR for the 3' flanking genomic sequence was conducted using Takara ExTaq PCR kit (Catalog #RR001A, Panvera, Madison, Wis.) in a 50 µl reaction volume containing a final concentration of 0.4 µM of Primer 281-9 and Primer 281-10. The reactions were performed using a GenAmp PCR System 9600 (Applied Biosystem, Foster City, Calif.) under the following cycling conditions: 1 cycle at 95° C. for 5 minute; 35 cycles of 94° C. for 30 seconds, 60° C. for 30 seconds, 72° C. for 60 second; 1 cycle at 72° C. for 10 minutes. The PCR products were separated using 1.0% agarose gel electrophoresis at 100 V for about 1 hour and visualized by ethidium bromide staining.

The 5' PCR product DNA sequence was determined resulting in a 603 nucleotide base pair sequence representing the 5' genomic/transgene insert sequence of cotton Cry1F event 281-24-236 and identified as SEQ ID NO:5. The 3' PCR product DNA sequence was determined resulting in a 562 nucleotide base pair sequence representing the 3' genomic/transgene insert sequence of cotton Cry1F event 281-24-236 and identified in SEQ ID NO:8.

The genomic/transgene junction sequences, SEQ ID NO:5 and SEQ ID NO:8 are novel DNA sequences in Cry1F event 281-24-236 that are diagnostic for cotton plant Cry1F event 281-24-236 and its progeny.

Example 3

Diagnostic Test for Cry1Ac Cotton Event 3006-210-23

The DNA extracted from the cotton leaf tissue was used in a PCR DNA amplification of the 5' genomic/transgene insert sequences in Cry1Ac event 3006-210-23 using primer 3006-20 (SEQ ID NO:9, 5'TTCCAACCTTTAACTATTATCCTGC3') and primer 3006-22 (SEQ ID NO:10, 5'GCTGCGGACATCTACATTTT3'), and the 3' genomic/transgene insert sequences flanking using primer 3006-9 (SEQ ID NO:12, 5'GACATGCAATGCTCATTATCTCTA3') and primer 3006-12 (SEQ ID NO:13, 5'AAGTCTCTGCCTTCTACCCTGG3'). The PCR DNA amplification analyses were conducted using genomic DNA extracted from cotton event Cry1Ac 3006-210-23 and non-transgenic cotton line PCS355. The amplification reaction for the 5' flanking genomic sequence was conducted using QIAGEN HotStarTaq PCR kit (catalog #203203 or 203205, QIAGEN, Valencia, Calif., USA) with a final concentration of 0.4 µM for Primer 3006-20 and Primer 3006-22 in a 50 µl reaction volume. The reactions were performed using a GenAmp PCR System 9600 (Applied Biosystem, Foster City, Calif.) under the following cycling conditions: 1 cycle at 95° C. for 15 minute; 35 cycles of 94° C. for 30 seconds, 53° C. for 30 seconds, 72° C. for 60 second; 1 cycle at 72° C. for 10 minutes. The PCR for the 3' flanking genomic sequence was conducted using QIAGEN HotStarTaq PCR kit (catalog #203203 or 203205, QIAGEN, Valencia, Calif., USA) in a 50 μl reaction volume containing a final concentration of 0.4 μM of Primer 3006-9 and Primer 3006-12. The reactions were performed using a GenAmp PCR System 9600 (Applied Biosystem, Foster City, Calif.) under the following cycling conditions: 1 cycle at 95° C. for 5 minutes; 30 cycles of 94° C. for 30 seconds, 56° C. for 30 seconds, 72° C. for 60 seconds; 1 cycle at 72° C. for 10 minutes. The PCR products were separated using 1.0% agarose gel electrophoresis at 100 V for about 1 hour and visualized by ethidium bromide staining.

The 5' PCR product DNA sequence was determined resulting in a 614 nucleotide base pair sequence representing the 5' genomic/transgene insert sequence of cotton Cry1Ac event 3006-210-23 (identified here as SEQ ID NO:11). The 3' PCR product DNA sequence was determined resulting in a 662 nucleotide base pair sequence representing the 3' genomic/transgene insert sequence of cotton Cry1Ac event 3006-210-23 (identified here as SEQ ID NO:14).

The genomic/transgene junction sequences, SEQ ID NO:11 and SEQ ID NO:14 are novel DNA sequences in Cry1Ac event 3006-210-23 that are diagnostic for cotton plant Cry1Ac event 3006-210-23 and its progeny.

Example 4

Further Diagnostic Tests

DNA event primer pairs are used to produce an amplicon diagnostic for Cry1F event 281-24-23 and Cry 1 Ac event 3006-210-23. These event primer pairs include, but are not limited to, SEQ ID NO:3 SEQ ID NO:4, SEQ ID NO:6, SEQ ID NO:7, SEQ ID NO:9, SEQ ID NO:10, SEQ ID NO:12, and SEQ ID NO:13. When used in a DNA amplification method (PCR), these primers produce an amplicon diagnostic for Cry1F event 281-24-236 and/or Cry1Ac event 3006-210-23, and their progenies. In addition to these primer pairs, further aspects of the subject invention include any primer pair derived from the amplicon product of SEQ ID NO:5, SEQ ID NO:9, SEQ ID NO:11, and/or SEQ ID NO:14 that, in a DNA amplification reaction, produces an amplicon diagnostic for Cry1F event 281-24-236, Cry1Ac event 3006-210-23, and their progenies. Any modification involving the use of DNA primers to produce an amplicon diagnostic for Cry1F event 281-24-236, Cry1Ac event 3006-210-23, and their progenies is within the ordinary skill of the art, given the benefit of the subject disclosure. The analysis of plant tissue sample from Cry1F event 281-24-236, Cry1Ac event 3006-210-23, and their progenies should include a positive tissue control from these events, a negative control from a cotton plant that is not any of these events, and a negative control that contains no template cotton DNA. Additional primer sequences can be derived from SEQ ID NO:1 and/or SEQ ID NO:2 by those skilled in the art of DNA amplification methods. Conditions optimized for the production of an amplicon may differ from the methods described in the Examples above. The use of these DNA primer sequences with modifications to the methods described in these Examples is within the scope of the invention. Amplicons and primers derived from SEQ ID NO:1 and/orSEQ ID NO:2 that are diagnostic for Cry1F event 281-24-236 and/orCry1Ac event 3006-210-23, and their progenies are aspects of the invention. The assay for amplicons of the Cry1F event 281-24-236, Cry1Ac event 3006-210-23, and their progenies can be performed by using a Stratagene Robocycler, MJ, Engine, or Mastercycler Gradient thermocycler, or by methods and apparatus known to those skilled in the art.

Having illustrated and described the principles of the present invention, it should be apparent to persons skilled in the art that the invention can be modified in arrangement and detail without departing from such principles. We claim all modifications that are within the spirit and scope of the appended claims.

The invention claimed is:

1. A method of detecting the presence of cry1F cotton event 281-24-236 in a sample comprising cotton DNA wherein said method comprises contacting said sample with
   a. a first primer that binds to a flanking sequence selected from the group consisting of residues 1-2074 of SEQ ID NO:1, residues 12,749-15,490 of SEQ ID NO:1, and complements thereof; and
   b. a second primer that binds to an insert sequence selected from the group consisting of residues 2075-12,748 of SEQ ID NO:1 and the complement thereof; and
subjecting said sample to polymerase chain reaction; and assaying for an amplicon, which spans the junction between said flanking sequence and said insert sequence, generated between said primers.

2. A method of detecting the presence of cry1Ac cotton event 3006-210-23 in a sample comprising cotton DNA wherein said method comprises contacting said sample with
   a. a first primer that binds to a flanking sequence selected from the group consisting of residues 1-527 of SEQ ID NO:2, residues 8,901-9,382 of SEQ ID NO:2, and complements thereof; and
   b. a second primer that binds to an insert sequence selected from the group consisting of residues 528-8,900 of SEQ ID NO:2, and the complement thereof; and
subjecting said sample to polymerase chain reaction; and assaying for an amplicon, which spans the junction between said flanking sequence and said insert sequence, generated between said primers.

3. The method of claim 1 wherein said second primer is selected from the group consisting of SEQ ID NO:4 and SEQ ID NO:6.

4. The method of claim 2 wherein said second primer is selected from the group consisting of SEQ ID NO:10 and SEQ ID NO:12.

5. A method of detecting the presence of a cotton event in a sample comprising cotton DNA wherein said method comprises contacting said sample with at least one polynucleotide, said polynucleotide comprising at least 30 nucleotides that hybridizes under stringent conditions with a sequence selected from the group consisting of residues 2060 to 2090 of SEQ ID NO:1, residues 12,733 to 12,765 of SEQ ID NO:1, residues 512-543 of SEQ ID NO:2, residues 8,885 to 8,916 of SEQ ID NO:2, and complements thereof; and wherein said method further comprises subjecting said sample and said polynucleotide to stringent hybridization conditions; and assaying said sample for hybridization of said polynucleotide to said DNA.

6. A DNA detection kit comprising a first primer that binds to a flanking sequence selected from the group consisting of residues 1-2074 of SEQ ID NO: 1, residues 12749-15490 of SEQ ID NO: 1, and complements thereof; and a second primer that binds to an insert sequence selected from the group consisting of residues 2075-12748 of SEQ ID NO; 1 and the complement thereof.

7. A DNA detection kit comprising a first primer that binds to a flanking sequence selected from the group consisting of residues 1-527 of SEQ ID NO: 2, residues 8901-9382 of SEQ ID NO: 2, and complements thereof; and a second primer that binds to an insert sequence selected from the group consisting of residues 528-8900 of SEQ ID NO: 2, and the complement thereof.

8. A DNA detection kit comprising a polynucleotide comprising at least 30 nucleotides that hybridizes under stringent conditions with a sequence selected from the group consisting of residues 2060 to 2090 of SEQ ID NO: 1, residues 12,733 to 12,765 of SEQ ID NO: 1, residues 512-543 of SEQ ID NO: 2, residues 8,885 to 8,916 of SEQ ID NO: 2, and complements thereof.

* * * * *

SEQUENCE LISTING

```
<160> NUMBER OF SEQ ID NOS: 21

<210> SEQ ID NO 1
<211> LENGTH: 15490
<212> TYPE: DNA
<213> ORGANISM: Artificial Sequence
<220> FEATURE:
<223> OTHER INFORMATION: Cry1F event 281-24-236 insert and its border
      sequences

<400> SEQUENCE: 1
aagcttgctt aaaagtatca caagccatga tccttataaa aatgatatct gacactatgc        60
ttctttgcac attcttcact atgctttctc atttgagcaa tggtgggatt tgctctcaaa       120
tttggtggcc ctatgtcagt attcaaaaat tttcataggt caaaggcttg aagataagcc       180
ttcattttta ccacccatat gtagtaaatt tcaccgatga atacaagagg tggaggtggt       240
gagaaactag atgaatacat tcttgcagaa aacgtccctc aaagatcaaa atggctctca       300
ataccaattc ttggtgtttt cagactaaga gagaaagcaa aacgagacaa tgaacccaca       360
agatgaatta atttcaatac attttttttaa atttcatttc aaacggttac aatatatacc       420
ttttgttttc caaacaactc aactgatcca actaacatct tggaaatagg aaaacttaac       480
ttgtacacaa actgattgtg aaatcaacac ctaaacacat caagtcatta ccaacttagt       540
```

```
ttattcctag ctaagtatct aacataagg attgaacaaa aggttaaacc aaaactttga    600
tttttttgct ctaggaagac agcttgcact tcatcataca gttcgcctta ttgttaatca    660
actcacactt tggctgtccg ttgatatgct ggcagttaaa atgttcacca atgtgcttag    720
acaatccgcc aagcctatcg tgtaaaaact ctttgcatga cagttcacct attgacagtc    780
cgccagtctt ttaatgctca gactgtctac catgtgactt agagacgaa ttgtttgcca     840 tatgtgttcg ccaactagat tgttcaccat ttgtgttgtt taccatgtgt gttcgctaat    900
gcatggttgg ccatgtcgca aaacaaattt tggatgggc caaaattgga atttttttcat    960 ttgaccaaat ataaaaaaac gaattgaaca aattactttt agagggatta aaaattaaaa   1020
ttatactatt tatcgagggg agtcaaggct cctatcttct tcgcttcttc tattgtttag    1080
attaagacta aaattttaaa atttatagaa attaaaattg atgaaattaa aatacaaaat   1140
taaatatata attcagttag gtttaaccat ttttaatgt tgcttagctt taatgtttgg    1200
gatttggcta ctttcagtcg ttatgcagtt atgctcagac aaatttgttc tctttctgtc    1260
ttatcaacta ctcaaaatct cagtatagtt atgtcattta atctcttcat cgtgagatgtt   1320 atattggtga aaatggggcc aagaaatcca cattcaatga ctttgaaaga atatatattg    1380
ttagttgcac attcccttat tcaatcacag ttgcttgttt ctgagtctat agaatcatga    1440
tatttgtaaa tcttatataa agtaagagta tatggctaga cagtctggcc ctgtcggctg    1500
aaggtaggga ggaattaatc aatcacagtt gcttgtttct gagtctatag aatcatgaat    1560
tttaaattta tggaatgcat ttttcgaag atattgtatg cattaagtgt aattttagtt     1620
tcaatatgaa atttgagatt tatatatata cttacataaa accctccttt actgaattag    1680
tgccatggat aaaagaccaa ttaagcaatc cttccaacac gtgcatgcac tggattttca    1740
tcgcctcgtc cattgttaaa ttgataggtt aataagaaca attagttggc tactgattat    1800
atggattctg ggttaaaagt atttaggttt actgttacat acatggagga tctacatcta    1860
ttttcacttt tgtttaatta atttaagtta gttttgatga gtttaaggat tgtactagcc    1920
aatagtagta cataaaggag atagagtacc aaaacaaaga aaaagccgaa aggtgttaat    1980
gctaaattgt aaaagaaagt taaaataaga gactcgaatt ataatatgat tctctggcgc    2040
actaattaag ctactatata ttgtcaatag tattgtaaat ggcttcatgt ccgggaaatc    2100
tacatggatc agcaatgagt atgatggtca atatggagaa aaagaaagag taattaccaa    2160 tttttttttca attcaaaaat gtagatgtcc gcagcgttat tataaaatga aagtacattt    2220
tgataaaacg acaaattacg atccgtcgta tttataggcg aaagcaataa acaaattatt    2280
ctaattcgga atctttatt tcgacgtgtc tacattcacg tccaaatggg ggccacttgg     2340
ctgcagtgca gcgtgacccg gtcgtgcccc tctctagaga taatgagcat tgcatgtcta    2400
agttataaaa aattaccaca tatttttttt gtcacacttg tttgaagtgc agtttatcta    2460
tctttataca tatatttaaa ctttactcta cgaataatat aatctatagt actacaataa    2520
tatcagtgtt ttagagaatc atataaatga acagttagac atggtctaaa ggacaattga    2580
gtattttgac aacaggactc tacagtttta tctttttagt gtgcatgtgt tctcctttt     2640 tttgcaaata gcttcaccta tataatactt catccatttt attagtacat ccatttaggg    2700
tttagggtta atggttttta tagactaatt ttttttagtac atctattta ttctatttta    2760 gcctctaaat taagaaaact aaaactctat tttagttttt ttatttaata atttagatat    2820
aaaatagaat aaaataaagt gactaaaaat taaacaaata ccctttaaga aattaaaaaa    2880
```

```
actaaggaaa cattttttctt gtttcgagta gataatgcca gcctgttaaa cgccgtcgac    2940
gagtctaacg gacaccaacc agcgaaccag cagcgtcgcg tcgggccaag cgaagcagac    3000
ggcacggcat ctctgtcgct gcctctggac ccctctcgag agttccgctc caccgttgga    3060
cttgctccgc tgtcggcatc cagaaattgc gtggcggagc ggcagacgtg agccggcacg    3120
gcaggcggcc tcctcctcct ctcacggcac cggcagctac ggggattcc tttcccaccg     3180
ctccttcgct ttcccttcct cgcccgccgt aataaataga caccccctcc acaccctctt    3240
tccccaacct cgtgttgttc ggagcgcaca cacacacaac cagatctccc ccaaatccac    3300
ccgtcggcac ctccgcttca aggtacgccg ctcgtcctcc ccccccccc cctctctacc     3360
ttctctagat cggcgttccg gtccatggtt agggcccggt agttctactt ctgttcatgt    3420
ttgtgttaga tccgtgtttg tgttagatcc gtgctgctag cgttcgtaca cggatgcgac    3480
ctgtacgtca gacacgttct gattgctaac ttgccagtgt ttctctttgg ggaatcctgg    3540
gatggctcta gccgttccgc agacgggatc gatttcatga ttttttttgt ttcgttgcat    3600
agggtttggt ttgcccttt cctttatttc aatatatgcc gtgcacttgt ttgtcgggtc     3660
atctttcat gctttttttt gtcttggttg tgatgatgtg gtctggttgg gcggtcgttc     3720
tagatcggag tagaattctg tttcaaacta cctggtggat ttattaattt tggatctgta    3780
tgtgtgtgcc atacatattc atagttacga attgaagatg atggatggaa atatcgatct    3840
aggataggta tacatgttga tgcgggtttt actgatgcat atacagagat gcttttttgtt   3900
cgcttggttg tgatgatgtg gtgtggttgg gcggtcgttc attcgttcta gatcggagta    3960
gaatactgtt tcaaactacc tggtgtattt attaattttg gaactgtatg tgtgtgtcat    4020
acatcttcat agttacgagt ttaagatgga tggaaatatc gatctaggat aggtatacat    4080
gttgatgtgg gttttactga tgcatataca tgatggcata tgcagcatct attcatatgc    4140
tctaaccttg agtacctatc tattataata aacaagtatg ttttataatt attttgatct    4200
tgatatactt ggatgatggc atatgcagca gctatatgtg gatttttta gccctgcctt     4260
catacgctat ttatttgctt ggtactgttt cttttgtcga tgctcaccct gttgtttggt    4320
gttacttctg caggtcgaca tgtctccgga gaggagacca gttgagatta ggccagctac    4380
agcagctgat atggccgcgg tttgtgtat cgttaaccat tacattgaga cgtctacagt     4440
gaactttagg acagagccac aaacaccaca agagtggatt gatgatctag agaggttgca    4500
agatagatac ccttggttgg ttgctgaggt tgagggtgtt gtggctggta ttgcttacgc    4560
tgggccctgg aaggctagga acgcttacga ttggacagtt gagagtactg tttacgtgtc    4620
acataggcat caaaggttgg gcctaggatc cacattgtac acacatttgc ttaagtctat    4680
ggaggcgcaa ggttttaagt ctgtggttgc tgttataggc cttccaaacg atccatctgt    4740
taggttgcat gaggctttgg gatacacagc ccgggtaca ttgcgcgcag ctggatacaa     4800
gcatggtgga tggcatgatg ttggtttttg gcaaagggat tttgagttgc cagctcctcc    4860
aaggccagtt aggccagtta cccagatctg agtcgacgga tccccgacat atgccccggt    4920
ttcgttgcga ctaacatgag ttcttggaca aatttgattg gacctgatga gatgatccaa    4980
cccgaggata tagcaaagct cgttcgtgca gcaatggaac ggccaaaccg tgcttttgtc    5040
cccaagaatg aggtgctatg catgaaggaa tctacccgtt gatgtccaac agtctcaggg    5100
ttaatgtcta tgtatcttaa ataatgttgt cggtattttg taatctcata tagattttca    5160
ctgtgcgacg caaaaatatt aaataaatat tattattatc tacgttttga ttgagatatc    5220
atcaatatta taataaaaat atccattaaa cacgatttga tacaaatgac agtcaataat    5280
```

```
ctgatttgaa tatttattaa ttgtaacgaa ttacataaag atcgaataga aaatactgca   5340
ctgcaaatga aaattaacac atactaataa atgcgtcaaa tatctttgcc aagatcaagc   5400
ggagtgaggg cctcatatcc ggtctcagtt acaagcacgg tatccccgaa gcgcgctcca   5460
ccaatgccct cgacatagat gccgggctcg acgctgagga cattgcctac cttgagcatg   5520
gtctcagcgc cggctttaag ctcaatccca tcccaatctg aatatcctat cccgcgccca   5580
gtccggtgta agaacgggtc tgtccatcca cctctgttgg gaattctgat cttggcggta   5640
cccgggggatc ctcattcctc catcagaagt aactccacgc tatcaacaat gaatgttcct   5700
tccgtttctc caatctcaat ccaaaccttg tcggtttctg gaaagtactc taactctttg   5760
gtgacatagc cggctggtaa cggtgtgtag tccccatagc ctctgttaga ttcgcaagga   5820
ttgtccctac gtccatcggt gtaagccttc tcctcatagg ctgatgcata gtcagcgggt   5880
acagaagagt tgctctcata ggctccatcg tatcctcgat tgcgagaagt gtaagtaccc   5940
tcatactcct cttgagtcgc agtgtagtca ttgcaagtta cggtgttgtt tgggtagact   6000
tcctcctcga cgcagttgct gaacttcagc tcgtcggtgt tgttctcaat ctcgtgtatg   6060
gtgacgcaac cttctccgta tccttctttg tacgcggtaa cacgaagaat gtagccacga   6120
ccaggacaga cacgaacttc ttgtgaaact tctgcttccc actcaggaac aacaaggaca   6180
gagcggtgat tgttctgttc ttctacatct acgtgccctt tcacattcca gcaggatagg   6240
ccattgttga agtcaccatt cttgatgaca ttcctcgcat catacaagga gaatgcagtg   6300
aagatgcgcc cttctaactc ttcaaagata gcagcattga caccggaat cacgctaagt   6360
tcaggaaggt aagcttcccg aatgctatga acgcgtttgt ctgcagcatg aatcatagct   6420
atgttggtat cagcttggag cctatcatac tgagagttca caaacagagc gtcaacgctt   6480
tctttggctt ctttgtacac aatgtttgtt tcccattcca acttctctct cttgtccctc   6540
cacttcttct cagccctctt cactctagcg agggcttctc caacaagtgg tttctcttct   6600
agaaactcca gattgcctag cctggcatgg ccatcttgag tcttgatctt gaagatcacc   6660
cacacaccga ggtcttcgtt caggtcggta cagccaacgt ctatgtccaa ggagaagtgg   6720
tgtgagtgat gggcacactt gccgatggga cttggggctg aaagtggcca gagtgaaccc   6780
gtcccaggca cattgactgt ctcatgtttg gcgttgtatc tgatgaggta gatctcaagg   6840
tcttgactgt cctcgatgta acctctcaac tggtatcttg tgtaggcttt gagtttcgat   6900
tcatctatct tctggtacag gtatgttgga tagcactcat caaaggtacc caagagcgta   6960
acatagttct ccttgaacac atcatcacct ccttgaatgg tgatgtccgt acttcccctc   7020
catccacgat ctagttgcct gttgatcccg cgaaagttgg gatcttgaag caagttccgc   7080
tcatcactaa gtcgcttagc atgtttgacc ttctcggaca actccttctt ctcatccaaa   7140
cagaactcat cagagaggca ctcaacaagg ttggaaacgc gatcgatgtg atagtcagtc   7200
acatctgtct tgagcccaat ctgattggac gaagtgaaca gagcattcac cgccttctgt   7260
gctcttttcca agtcagactc tgcctcgagt gtggcagtaa ctggaatcaa ctcaaacctg   7320
tcaatgtaca cttcgttgcc tgaactgaag gtatcagcac ctactgtgaa actgctctgg   7380
ctcattggaa aggtgaacgc ggtgttgata gtggcgtagg agaaagattg gaatgtaagt   7440
ggatcaccgg tatccattgt cttgttgaac tgaccagcaa agatccgttc acctgcaacc   7500
gtaacgtaga ttcttagatt ggtagtagag gcatagcgta tcctggcacg atacctttgg   7560
ggaagttgcc cattgatgtt gacaatggtg tacgcgaatg gtcctccact agtgcgtcga   7620
```

```
agaatgtctc ctcccgtgaa ccccggccct cttacaactg tagttcctga ctgaagtgtg    7680
tgtgccttca ccaagggaat ctgagtgatt ctctctggat caatggtgtt tgtgggggta    7740
gcgctacgat gcgtccaaga gaacattggt gctctccatg agtcggaacc tgagatctca    7800
cctggccagc gcacaaaggt aacatgattc agcacatggg agtagtcatt ccaaggtgcg    7860
ccgctgttgt cttgaggtgg tatctcatct agagagtcaa tggtcccgga gttcctgaat    7920
gtgcgggtgt gattcgtacc agtttgttga aaggccactc ccctaagacc gagtacatag    7980
tgaggattgc caaagcctcc tcggacgaag acaggatctg acaaggtccg atagaaagga    8040
cgtggatctt catctgcaat ccagatggcg ccccgggat tgaagacccc gtaactagga     8100
aagttgatac gattgccagc cgtgttgcgt gagctaacta agtgtcctcc ccacacagtt    8160
tgggatctaa cagtctctgc agtcacaaac aaagagttca tgaagtccat gagatggggt    8220
ggtctgactc caaactcagc cctgttgaaa ccattgggta tgttcgcaga aactggagag    8280
tcttcaatga ctgaactggt gtagatctcc cttgtaagtt gggatgacgt ttgaatcgga    8340
taggtacgaa catcgtagtt cggaaagaga gcaactatgt ctaacacagt aagtgtaagg    8400
tctctcctga actgattgaa cctggcccat tggcgagtgt tagtacctct caggttctcc    8460
aatccctgat tgtaggtatc caaacaatgt ttcgtgtatc gatgaatcag attgatgagt    8520
ctgttgtagt gattgttgac agtagctatg tccagtcccc aaccttgccc aaacgacaca    8580
gcgtcgcgca gtagtgacaa gtgcaggtta gcagcttgaa catagaccga gagaagaggg    8640
atctcgaagc tggtaagggt gaagttgttg atggctgtga tcaaagcatc atctgtgtta    8700
gcaaagcgta tacgcacatc ttctctcagt tgggcattgt taggattggc ttcccactct    8760
cttagtgctt caatgtagat ctcatagctg tctgctaagc cacgaagggt agtgatggcc    8820
cgattccttt ccaaggtctc aatcctttgt tcaatcaact gttcaatctg gagaagaaag    8880
aggctccaat cagatggagt gatgaagccc cagatgaggt cgaagaggcc aaacgcaact    8940
cccacacctg gaacaaactc agacaacagg agacgtgtaa gggacaggga gatgtctaac    9000
ggcaatctgc cagtcgacct ctcttcgttg agaatctcta cttcaggatt gttgaggcag    9060
ttgtagggga cgcactgatt ctgtatgttg ttctccattg ttggatccgc gatttggtgt    9120
atcgagattg gttatgaaat tcagatgcta gtgtaatgta ttggtaattt gggaagatat    9180
aataggaagc aaggctattt atccatttct gaaaaggcga aatggcgtca ccgcgagcgt    9240
cacgctctag tcgaccatgt acgtaagcgc ttacgttttt ggtggacccc ctcgaccatg    9300
tacgtaagcg cttacgtttt tggtggaccc cctcgaccat gtacgtaagc gcttacgttt    9360
ttggtggacc ccctcgacca tgtacgtaag cgcttacgtt tttggtggac cccctcgacg    9420 gatccccct cgaccctaga cgtatctatt caaaagtcgt taatggctgc ggatcaagaa     9480
aaagttggaa tagaaacaga atacccgcga aattcaggcc cggttgccat gtcctacacg    9540
ccgaaataaa cgaccaaatt agtagaaaaa taaaaactga ctcggatact tacgtcacgt    9600
cttgcgcact gatttgaaaa atctcaatat aaacaaagac ggccacaaga aaaaaccaaa    9660
acaccgatat tcattaatct tatctagttt ctcaaaaaaa ttcatatctt ccacaccctc    9720
gagatctaga tatcgatgaa ttttggcgcg ccttaattaa ggaattcctc gagtttaaac    9780
ggatccctga aagcgacgtt ggatgttaac atctgcaaat tgccttttct tatcgaccat    9840
gtacgtaagc gcttacgttt ttggtggacc cttgaggaaa ctggtagctg ttgtgggcct    9900
gtggtctcaa gatggatcat taatttccac cttcacctac gatgggggc atcgcaccgg     9960 tgagtaatat tgtacggcta agagcgaatt tggcctgtag acctcaattg cgagctttct    10020
```

```
aatttcaaac tattcgagct ttctaattga atatatccag ggcccagcgt aagcaatacc   10080
agccacaaca ccctcaacct cagcaaccaa ccaagggtat ctatcttgca acctctctag   10140
atcatcaatc cactcttgtg gtgtttgtgg ctctgtccta aagttcactg tagacgtctc   10200
aatgtaatgg ttaacgatat cacaaaccgc ggccatatca gctgctgtag ctggcctaat   10260
ctcaactggt ctcctctccg gagacatgtc gacctgcaga agtaacacca acaacaggg    10320 tgagcatcga caaagaaac agtaccaagc aaataaatag cgtatgaagg cagggctaaa    10380
aaaatccaca tatagctgct gcatatgcca tcatccaagt atatcaagat caaaataatt   10440
ataaaacata cttgtttatt ataatagata ggtactcaag gttagagcat atgaatagat   10500
gctgcatatg ccatcatgta tatgcatcag taaaacccac atcaacatgt atacctatcc   10560
tagatcgata tttccatcca tcttaaactc gtaactatga agatgtatga cacacacata   10620
cagttccaaa attaataaat acaccaggta gtttgaaaca gtattctact ccgatctaga   10680
acgaatgaac gaccgcccaa ccacaccaca tcatcacaac caagcgaaca aaaagcatct   10740
ctgtatatgc atcagtaaaa cccgcatcaa catgtatacc tatcctagat cgatatttcc   10800
atccatcatc ttcaattcgt aactatgaat atgtatggca cacacataca gatccaaaat   10860
taataaatcc accaggtagt ttgaaacaga attctactcc gatctagaac gaccgcccaa   10920
ccagaccaca tcatcacaac caagacaaaa aaagcatga aaagatgacc cgacaaacaa    10980
gtgcacggca tatattgaaa taaaggaaaa gggcaaacca aaccctatgc aacgaaacaa   11040
aaaaaatcat gaaatcgatc ccgtctgcgg aacggctaga gccatcccag gattcccaa    11100 agagaaacac tggcaagtta gcaatcagaa cgtgtctgac gtacaggtcg catccgtgta   11160
cgaacgctag cagcacggat ctaacacaaa cacggatcta acacaaacat gaacagaagt   11220
agaactaccg ggccctaacc atggaccgga acgccgatct agagaaggta gagaggggg    11280 gggggggggg aggacgagcg gctgtacctt gaagcggagg tgccgacggg tggatttggg   11340
ggagatctgg ttgtgtgtgt gtgcgctccg aacaacacga ggttggggaa agagggtgtg   11400 gaggggggtgt ctatttatta cggcgggcga ggaagggaaa gcgaaggagc ggtgggaaag  11460 gaatccccg tagctgccgg tgccgtgaga ggaggaggag gccgcctgcc gtgccggctc    11520
acgtctgccg ctccgccacg caatttctgg atgccgacag cggagcaagt ccaacggtgg   11580
agcggaactc tcgagagggg tccagaggca gcgacagaga tgccgtgccg tctgcttcgc   11640
ttggcccgac gcgacgctgc tggttcgctg gttggtgtcc gttagactcg tcgacggcgt   11700
ttaacaggct ggcattatct actcgaaaca agaaaaatgt ttccttagtt tttttaattt   11760 cttaagggt atttgcttaa ttttagtca ctttatttta ttctatttta tatctaaatt    11820
attaaataaa aaaactaaaa tagagtttta gttttcttaa tttagaggct aaaatagaat   11880
aaaatagatg tactaaaaaa attagtctat aaaaaccatt aaccctaaac cctaaatgga   11940
tgtactaata aaatggatga agtattatat aggtgaagct atttgcaaaa aaaaaggaga   12000
acacatgcac actaaaaaga taaaactgta gagtcctgtt gtcaaaatac tcaattgtcc   12060
tttagaccat gtctaactgt tcatttatat gattctctaa aacactgata ttattgtagt   12120
actatagatt atattattcg tagagtaaag tttaaatata tgtataaaga tagataaact   12180
gcacttcaaa caagtgtgac aaaaaaaata tgtggtaatt ttttataact tagagatgca   12240
atgctcatta tctctagaga ggggcacgac cgggtcacgc tgcactgcag ccaagtggcc   12300
cccatttgga cgtgaatgta gacacgtcga aataagatt tccgaattag aataatttgc    12360
```

-continued

```
ttattgcttt cgcctataaa tacgacggat cgtaatttgt cgctttatca gaatgtactt    12420
tcattttata ataacgctgc ggacatctac attttgaat tgaaaaaaaa ttggtaatta    12480
ctctttcttt ttctccatat tgaccatcat actcattgct gatccatgta gatttcctt    12540 acttgtctcc ctctaatctg actttattaa cccaaagcaa ttgcttattt gttccccacg    12600
cccacaaagc ccagcattgt ccctaaggta ttaatttgtt gttcgattct tgttcttgaa    12660
cccatttgga gaatgcaaca agggttttca tgtcagcacg gtaatggttc tgtgtaaatt    12720
ccagtagtgc tgcccaagta aagtctgggt atttcctcga atttgcggca ttaactaagc    12780
tagctgctgg tgtcaccggt ctctccagct cgggacatag aaagaatgca agtgattttc    12840
tcaccgtttc agtattcact actgcccaag cagctcttgt agataccgtt tgtcaaagcc    12900
tgtattcaaa caccacaacc tcattttcgt taaaatttt tgtatatacg tatgcatata    12960
tgttcagaat gtttattacc atgaatgtat cgcaatgttg acaacgaaag ctcctgggat    13020
atgagcaacg gagtgccact tttcatcggc aaacacttga aggcctccaa cttgatcctg    13080
atgaaggatt gtcaaggaag tgggatcggt gtggggaccg gttcccaggg tcaactcagg    13140
cttttcgcat ggagagtagt gattcagtct caggattgaa tcattttgtt cgaaaaagtc    13200
tttgaagtag gcttggtcaa gccctagact tatccctagc agccccatta tctctttgga    13260
aaccttgttc ctggcttcac aatattcctg gtaaagcctc ctgtcaagta cgaaaagcaa    13320
aatcgagtgt tagattccta tcctatggta aaacttgtcg caacattcta caaattaaca    13380
taggttataa aagagaaacg caaagtcaaa aaaggccatc cagttataat gtgtattttt    13440
tgttttagga aagggtat ttaagcaatc catgttgaat ggacttaggg ttcggtcaat    13500
gcaaggaatg atgtctattg aatttgtcac cccatctctt tcaaacctaa aaagatgta    13560 tatccaattg tcactatttg tacaaggctt gaaatacaca tgggggttaac aaatacgctg    13620 aaactgcaac atgtattttt tgcattttgg agactaaatc ttgacgtaaa ataagctga    13680 tcatctcgta tattgactga atgcaaatta gcatttctcc tatttaatta ggaatggaag    13740
ggtgagaaga atttatttac ccaaaatctc taaaatcttc agtgccgaaa agacagtgtt    13800
tctttccatg gcaacttgga ggaaaacctg ccaacgaaac tgcttgcata cccatagctt    13860
tctcctactt ttctcttagc cttttgcttc tcagagagtt gcaggctgaa gaagcggtcc    13920
atgtactgat gagcttacaa ccaaaaaaaa cccatgcttc ttgcatgcct cattcaccgc    13980
ccctgccact tttgatacag caagagagcc cccaagcaag aaagctccca agtcaatggc    14040
ttgaattaca agttccgggt catccaggca tggcttatcg tcgtcaggcc atatgaactg    14100
agagggtata ttggattcag atccaaggat tgatgcatcg aaagctaaag ggcgatgctc    14160
attctttgcg acagcagcag ttggcggaag catcggcttc tcttgaatga cagaaactat    14220
tggcagacaa tgtaccattt tctgtttctt gttttaggtg gtcggagagg aaaaagaaga    14280
caagatatag aggagcaaaa ctaagagggt ttaaataaga gaagtagaaa accaataata    14340
tttggaatct aattgtttgt tttgaactgt tgcctcattt ccccttttaat ttgtgttgtg    14400 ttgcagcttt aacgcttcct ttgggttcga ttgcaatata gtgcgttgaa attttacct    14460 tgatttttcaa tctcactaca ccacagtgac ttgcttggtt gtttggataa tttttacctt    14520
gattttcaat ctcactacac cacagtgact tgcttggttg tttggataat ttttaccttg    14580
attttcaatc tcactacacc acagtgactt gcctggttgt ttggatatct tggtttccag    14640
cacagtgaga caagcctgct gcactcgaca accttatctt cactggtgct aaaagctcca    14700
gtcagctcta gctagggcaa taggtatttt tggatgacaa aaatacccat actttaattt    14760
```

-continued

```
attattttac catttttatcc ttagatgtta aactaatttc tttcccaatc ttatttgttt    14820
tcagatttgg gaataaaaca atagtttctc ccttgttctt gctggtttct cccttgttct    14880
tgctggtttc tcccctcttt tttgctttgt tcttggttgt gggagcttag gatattcttt    14940
ttcttcaatc agactaacaa gttagagata tcttgtgttt tttcacttta ttttctcatg    15000
ctcaacattt acccttttc tcaattaaca ggggaagtct acattaatta gtgcactctc    15060
agatagtaat ctgtatagtg atgcaatgta tatatattct ttaaaacagt ttttcctcga    15120
agttaaattc tttgttaaaa gtaaaaggct ggatgttttt acctaattgg aggtaatgtc    15180
tttgtgtaga ttgtttgcaa cattggatgg ttgattaaaa agtgttgttc ttccttcaag    15240
gtgagatggt ttgctgtcac tcactattat tattgttgtt attgttattg cttttccatt    15300
gaatagcctg gttctaaatg atatacttac cttatcccat aggcagcaac attttatctt    15360
ttgatctttg gacctatcat ttagcatgct ttacactcta tttagtaata ttattactaa    15420
ctataatttt aagtcataca caatgaaatt acctaaacat ctaaactcaa aaaattataa    15480
cttaaagctt                                                           15490
```

<210> SEQ ID NO 2
<211> LENGTH: 9382
<212> TYPE: DNA
<213> ORGANISM: Artificial Sequence
<220> FEATURE:
<223> OTHER INFORMATION: Cry1Ac event 3006-210-23 insert and its border
      sequences
<220> FEATURE:
<221> NAME/KEY: misc_feature
<222> LOCATION: (556)..(556)
<223> OTHER INFORMATION: n is a, c, g, or t

<400> SEQUENCE: 2

```
accaattatt atcgtctttt ttaattattc caacctttaa ctattatcct gccttaaaat      60
tcgaatacat ttattatcta taaactatcc gaatattatt atctaaatcc taattaaata     120 ctattttta tcgagtattc gtatccgcca aggaaatcca tctccaaatt ttcaattatt     180
tttcagatat ctaaatctgt aaaatttcaa attcaagtac gttacaattc tttataaata     240
atccaaatta taaatatttt ataactatta attcataaat taaaatttat tattcaaata     300
ttcgaataat ctattttaa gacgtaaagt attacatcga agggttactt tcaaagggta     360
gtgtatttcc atttcaatta ttcagaacgt tgtcgttttg ttccggtcat agaaaagggc     420
tctggaagag aagaaaatga cttgactttt caatttcatg ctcatccact cgtttcaatt     480
actgtttact aaaaaaataa taaaataaaa tattaacaat gcattgagta tgatgtccgg     540 gaaatcaca tggatnagca atgagtatga tggtcaatat ggagaaaaag aaaagagtaat     600 taccaattttt ttttcaattc aaaaatgtag atgtccgcag cgttattata aaatgaaagt     660
acattttgat aaaacgacaa attacgatcc gtcgtattta taggcgaaag caataaacaa     720
attattctaa ttcggaaatc tttatttcga cgtgtctaca ttcacgtcca atggggggcc     780
acttggctgc agccaagctt tcgcgagctc gagatccccg acatatgccc cggtttcgtt     840
gcgactaaca tgagttcttg gacaaatttg attggacctg atgagatgat ccaacccgag     900
gatatagcaa agctcgttcg tgcagcaatg gaacggccaa accgtgcttt tgtccccaag     960
aatgaggtgc tatgcatgaa ggaatctacc cgttgatgtc caacagtctc agggttaatg    1020
tctatgtatc ttaaataatg ttgtcggtat tttgtaatct catatagatt ttcactgtgc    1080
gacgcaaaaa tattaaataa atattattat tatctacgtt ttgattgaga tatctagatc    1140
```

```
tcgaggtgtg aagatatga atttttttga gaaactagat aagattaatg aatatcggtg      1200
ttttggtttt ttcttgtggc cgtctttgtt tatattgaga ttttttcaaat cagtgcgcaa    1260
gacgtgacgt aagtatccga gtcagttttt attttctac taatttggtc gtttatttcg      1320
gcgtgtagga catggcaacc gggcctgaat tcgcgggta ttctgtttct attccaactt      1380
tttcttgatc cgcagccatt aacgactttt gaatagatac gtctagggtc gagggggat      1440
ccgtcgaggg ggtccaccaa aaacgtaagc gcttacgtac atggtcgagg gggtccacca     1500
aaaacgtaag cgcttacgta catggtcgag gggtccacc aaaaacgtaa gcgcttacgt      1560
acatggtcga ggggtccac caaaaacgta agcgcttacg tacatggtcg actagagcgt      1620
gacgctcgcg gtgacgccat ttcgcctttt cagaaatgga taaatagcct tgcttcctat     1680
tatatcttcc caaattacca atacattaca ctagcatctg aatttcataa ccaatctcga     1740
tacaccaaat cgcggatccg tcgacctgca ggtcgacatg tctccggaga ggagaccagt    1800
tgagattagg ccagctacag cagctgatat ggccgcggtt tgtgatatcg ttaaccatta    1860
cattgagacg tctacagtga actttaggac agagccacaa acaccacaag agtggattga   1920
tgatctagag aggttgcaag atagataccc ttggttggtt gctgaggttg agggtgttgt    1980
ggctggtatt gcttacgctg ggccctggaa ggctaggaac gcttacgatt ggacagttga    2040
gagtactgtt tacgtgtcac ataggcatca aaggttgggc ctaggatcca cattgtacac    2100
acatttgctt aagtctatgg aggcgcaagg ttttaagtct gtggttgctg ttataggcct    2160
tccaaacgat ccatctgtta ggttgcatga ggctttggga tacacagccc ggggtacatt    2220
gcgcgcagct ggatacaagc atggtggatg catgatgtt ggtttttggc aaagggattt     2280
tgagttgcca gctcctccaa ggccagttag gccagttacc cagatctgag tcgacggatc    2340
cccgacatat gccccggttt cgttgcgact aacatgagtt cttggacaaa tttgattgga    2400
cctgatgaga tgatccaacc cgaggatata gcaaagctcg ttcgtgcagc aatggaacgg    2460
ccaaaccgtg cttttgtccc caagaatgag gtgctatgca tgaaggaatc tacccgttga    2520
tgtccaacag tctcagggtt aatgtctatg tatcttaaat aatgttgtcg gtatttgta    2580
atctcatata gattttcact gtgcgacgca aaatattaa ataaatatta ttattatcta    2640
cgttttgatt gagatatcat caatattata ataaaaatat ccattaaaca cgatttgata    2700
caaatgacag tcaataatct gatttgaata tttattaatt gtaacgaatt acataaagat    2760
cgaatagaaa atactgcact gcaaatgaaa attaacacat actaataaat gcgtcaaata    2820
tctttgccaa gatcaagcgg agtgagggcc tcatatccgg tctcagttac aagcacggta   2880
tcccgaagc gcgctccacc aatgccctcg acatagatgc cgggctcgac gctgaggaca    2940
ttgcctacct tgagcatggt ctcagcgccg gctttaagct caatcccatc ccaatctgaa    3000
tatcctatcc cgcgcccagt ccggtgtaag aacgggtctg tccatccacc tctgttggga   3060
attctgatct tggcgcgcat gcggatcctc attcctccat cagaagtaac tccacgctat    3120
caacaatgaa tgttccttcc gtttctccaa tctcaatcca aaccttgtcg gtttctggaa    3180
agtactctaa ctctttggtg acatagccgg ctggtaacgg tgtgtagtcc ccatagcctc   3240
tgttagattc gcaaggattg tccctacgtc catcggtgta agccttctcc tcataggctg    3300
atgcatagtc agcgggtaca gaagagttgc tctcataggc tccatcgtat cctcgattgc   3360
gagaagtgta agtaccctca tactcctctt gagtcgcagt gtagtcattg caagttacgg    3420
tgttgtttgg gtagacttcc tcctcgacgc agttgctgaa cttcagctcg tcggtgttgt    3480
```

```
tctcaatctc gtgtatggtg acgcaacctt ctccgtatcc ttctttgtac gcggtaacac   3540
gaagaatgta gccacgacca ggacagacac gaacttcttg tgaaacttct gcttcccact   3600
caggaacaac aaggacagag cggtgattgt tctgttcttc tacatctacg tgcccttttca  3660 cattccagca ggataggcca ttgttgaagt caccattctt gatgacattc ctcgcatcat   3720
acaaggagaa tgcagtgaag atgcgccctt ctaactcttc aaagatagca gcattgacac   3780
ccggaatcac gctaagttca ggaaggtaag cttcccgaat gctatgaacg cgtttgtctg   3840
cagcatgaat catagctatg ttggtatcag cttggagcct atcatactga gagttcacaa   3900
acagagcgtc aacgctttct ttggcttctt tgtacacaat gtttgtttcc cattccaact   3960
tctctctctt gtccctccac ttcttctcag ccctcttcac tctagcgagg gcttctccaa   4020
caagtggttt ctcttctaga aactccagat tgcctagcct ggcatggcca tcttgagtct   4080
tgatcttgaa gatcacccac acaccgaggt cttcgttcag gtcggtacag ccaacgtcta   4140
tgtccaagga gaagtggtgt gagtgatggg cacacttgcc gatgggactt ggggctgaaa   4200
gtggccagag tgaacccgtc ccaggcacat tgactgtctc atgtttggcg ttgtatctga   4260
tgaggtagat ctcaaggtct tgactgtcct cgatgtaacc tctcaactgg tatcttgtgt   4320
aggctttgag tttcgattca tctatcttct ggtacaggta tgttggatag cactcatcaa   4380
aggtacccaa gagcgtaaca tagttctcct tgaacacatc atcacctcct tgaatggtga   4440
tgtccgtact tcccctccat ccacgatcta gttgcctgtt gatcccgcga agttgggat    4500 cttgaagcaa gttccgctca tcactaagtc gcttagcatg tttgaccttc tcggacaact   4560
ccttcttctc atccaaacag aactcatcag agaggcactc aacaaggttg gaaacgcgat   4620
cgatgtgata gtcagtcaca tctgtcttga gcccaatctg attggacgaa gtgaacagag   4680
cattcaccgc cttctgtgct cttccaagt cagactctgc ctcgagcgtt gcagtaacgg     4740
gaatgaattc gaagcggtcg attatcactc cggcggttcc ggagaaattt ctaacaccta   4800
ctatgttacc tagggaagag gtgaaggcat tggcactttc gaagtaaccg aaatcgctag   4860
attggagatt atccaaggat gtagctgtcg ctggtactgt attggaaaag atggaggaat   4920
taccccaatt gacgttgagg tgaatagggg taacagaggc ataccttaca cgaacacgat   4980
atctggtaga tgtcgatggg aagtgaatgg gcacttcaat ataccctcta ttctggatgt   5040
tgttgccgga agaattcagc ctaaccaagt cgcctccagt gaatcctggt cctgaaatga   5100
cagaaccatt aaagagaaag ttccccttga cagctgggat ctgagtaatg ctatcggatg   5160
caattatgtt gttaaactca gcactacgat gtatccaaga gaacatcgga gctctgatga   5220
tactaacgct gctattacta aagcctgaac ggaacatgga cacatggcta aggcgatggc   5280
taaacccttg cctaggtgga acgttgttgt tctgtggagg gatctcatcc aagctatcaa   5340
ctgttccgct ctttctgtag acagcggatg gcagatttga ggaggttcca taggcaaatt   5400
ctgtcccgtc aagcacagac aattgttgat tgttgatgcc gatgttgaaa ggtctcctat   5460
atagagtgct ggacaaggtt ctatacacgc cctgaccgag ttgagcaaca atacgttgtt   5520
gtggagctgc attgcccata gtcccgtaaa gtgggaaagt gaattctggt ccagagaacc   5580
caacgggtga tgccatgatc tgatgccctg accagtagta ataaccgcgg tgcgcatcgg   5640
tgtagatcgt gatactgttc aatatgtcca tcaggtgtgg agacctgatg cttctctcta   5700
tgccctgagc cgagcctcga aagctaccgt cgaagttctc gaggactggg tttgtgtaga   5760
tttcccgggt caattgtgac acagtacgga ttgggtagcg cctagagtcg tagttgggaa   5820
agagagcgac aatgtctagg acagttagtg tcaactctcg cctgaactgg ttgtacctga   5880
```

-continued

```
cccaatctct agaatccggt ccccagacac gttcgagacc cgtgttgtac cagcgaacag    5940
cataatcggt atagttgcca ataagcctag tcagatcatt ataacgacta ttgatagttg    6000
cggcatcaaa gccccaccgt tgtccgaaca cggagacatc gcggagcacc gacaagtgca    6060
ggttggcagc ctgcacgtac acggataaaa gaggaacttg gtaattctga acggcgaaga    6120
gcggaattgc ggtcgtcagc gcgctgttca tgtcattgaa ttgaatgcgc atctcctctc    6180
ttaaggcagg attggtcggg tctgcttccc actctcgaaa agattctgcg taaatctggt    6240
aaaggttgct gaggccttct aaccttgaga tggcttggtt cctagcgaat tcttctattc    6300
tttggttaat taactgctct atctgtacaa gaaaggcgtc ccattgagag ggaccaaaga    6360
ttccccaaat gatatcgaca agtccaagca cgaatccagc accgggcacg aactctgaca    6420
aaaggaattg ggtaagtgac aacgagatgt cgataggtgt gtaaccagtc tcaatccgtt    6480
ctccacccag cacctcaacc tcaggggttgc tcaggcagtt gtaaggaatg cactcgttga    6540
tgttgggatt gttgtccatt gttggatcct ctagagtcga cctgcagaag taacaccaaa    6600
caacagggtg agcatcgaca aaagaaacag taccaagcaa ataaatagcg tatgaaggca    6660
gggctaaaaa aatccacata tagctgctgc atatgccatc atccaagtat atcaagatca    6720
aaataattat aaaacatact tgtttattat aatagatagg tactcaaggt tagagcatat    6780
gaatagatgc tgcatatgcc atcatgtata tgcatcagta aaacccacat caacatgtat    6840
acctatccta gatcgatatt tccatccatc ttaaactcgt aactatgaag atgtatgaca    6900
cacacataca gttccaaaat taataaatac accaggtagt ttgaaacagt attctactcc    6960
gatctagaac gaatgaacga ccgcccaacc acaccacatc atcacaacca agcgaacaaa    7020
aagcatctct gtatatgcat cagtaaaacc cgcatcaaca tgtataccta tcctagatcg    7080
atatttccat ccatcatctt caattcgtaa ctatgaatat gtatggcaca cacatacaga    7140
tccaaaatta ataaatccac caggtagttt gaaacagaat tctactccga tctagaacga    7200
ccgcccaacc agaccacatc atcacaacca agacaaaaaa aagcatgaaa agatgacccg    7260
acaaacaagt gcacggcata tattgaaata aaggaaaagg gcaaaccaaa ccctatgcaa    7320
cgaaacaaaa aaaatcatga aatcgatccc gtctgcggaa cggctagagc catcccagga    7380
ttccccaaag agaaacactg gcaagttagc aatcagaacg tgtctgacgt acaggtcgca    7440
tccgtgtacg aacgctagca gcacggatct aacacaaaca cggatctaac acaaacatga    7500
acagaagtag aactaccggg ccctaaccat ggaccggaac gccgatctag agaaggtaga    7560
gagggggggg gggggaggac gagcggcgta ccttgaagcg gaggtgccga cgggtggatt    7620
tgggggagat ctggttgtgt gtgtgtgcgc tccgaacaac acgaggttgg ggaaagaggg    7680
tgtggagggg gtgtctattt attacggcgg gcgaggaagg gaaagcgaag gagcggtggg    7740
aaaggaatcc cccgtagctg ccggtgccgt gagaggagga ggaggccgcc tgccgtgccg    7800
gctcacgtct gccgctccgc cacgcaattt ctggatgccg acagcggagc aagtccaacg    7860
gtggagcgga actctcgaga ggggtccaga ggcagcgaca gagatgccgt gccgtctgct    7920
tcgcttggcc cgacgcgacg ctgctggttc gctggttggt gtccgttaga ctcgtcgacg    7980
gcgtttaaca ggctggcatt atctactcga aacaagaaaa atgtttcctt agttttttta    8040
atttcttaaa gggtatttgt ttaattttta gtcactttat tttattctat tttatatcta    8100
aattattaaa taaaaaaact aaatagagtt tttagttttc ttaatttaga ggctaaaata    8160
gaataaaata gatgtactaa aaaaattagt ctataaaaac cattaaccct aaaccctaaa    8220
```

```
tggatgtact aataaaatgg atgaagtatt atataggtga agctatttgc aaaaaaaaag    8280
gagaacacat gcacactaaa aagataaaac tgtagagtcc tgttgtcaaa atactcaatt    8340
gtcctttaga ccatgtctaa ctgttcattt atatgattct ctaaaacact gatattattg    8400
tagtactata gattatatta ttcgtagagt aaagtttaaa tatatgtata aagatagata    8460
aactgcactt caaacaagtg tgacaaaaaa aatatgtggt aatttttat aacttagaca     8520 tgcaatgctc attatctcta gagaggggca cgaccgggtc acgctgcact gcaggcatgc    8580
gcgccttaat taaggaattc ctcgagttta acggatccc tgaaagcgac gttggatgtt     8640
aacatctaca aattgccttt tcttatcgac catgtacgta agcgcttacg tttttggtgg    8700
acccttgagg aaactggtag ctgttgtggg cctgtggtct caagatggat cattaatttc    8760
caccttcacc tacgatgggg ggcatcgcac cggtgagtaa tattgtacgg ctaagagcga    8820
atttggcctg tagacctcaa ttgcgagctt tctaatttca aactattcgg cctaacttt     8880 tggtgtgatg atgctgactg gcttacgtgt ggaaaaaatt tgcaatctat gtagtcttta    8940
actaatgttt ttttctttaa aaaaaagtc attattttg gtttgattaa tatatttggt      9000
ttaaattaaa taaatatta aaagtttag ttaaatcatc tatttaaacg atttgtactg      9060
atttgtgatc tattaattt ttaacttaat ctagaccagg gtactagttg gtccgatccc     9120
atcttgaaaa cactatcttt agcttgctgg taggttccag ggtagaaggc agagactttt    9180
ttggagggtt tttattatta aatttatatt tttataattt ttaaatgatt aaaataaaaa    9240
tttattattt taagaggaga taagtgcaa ttttaccata tattaattta aaattttata     9300
aatttaaaaa agaaaaaaac taaaatttta attttatagg ttctaaaata ataaatataa    9360
cttactgagt tttttaagc tt                                              9382

<210> SEQ ID NO 3
<211> LENGTH: 10348
<212> TYPE: DNA
<213> ORGANISM: Artificial Sequence
<220> FEATURE:
<223> OTHER INFORMATION: Cry1Ac event 3006-48-81 insert and its border
      sequences
<220> FEATURE:
<221> NAME/KEY: misc_feature
<222> LOCATION: (664)..(664)
<223> OTHER INFORMATION: n is a, c, g, or t

<400> SEQUENCE: 3
gaatcaatct tttacgggaa aactcaattg gaatgaaact tgtttccagt aaaagtatta     60
aaaaatgtat aaactagtcc atgtatgata gtgtaaagag tatattggag ttaaaaattt    120
catcccatgt tactctatat tacattataa aggaagctat aggttggctc actgcaccac    180
ccaatcaaga tactcatatg tattacttaa tatataatat taaaagatat catttctttt    240
tgttatcaga ttaaagagaa ctaagatatt acaaacttgc aaaacaatag ttaggccaac    300
ccatatttta aatattttct tctttttct actcaaacct attttgtttc caaatattga     360
agagttctgt tctgattgga tatactctcg gacaagttta actctaaatt ttccaaatat    420
tgaaatatgg atttgctcac atggaaaaac ggttcttgaa caataaatca aaatagcata    480
ttctatcaat ggaatcaagg aattccatat tcatttcaaa gttggagcca agcatgcatg    540
ataatgattt atagcaattt tgtcaaaagg aaaaaataag gtgattggat gacaagaaac    600
aaagggaaaa tgaattaaca gcctgcattt aatatcattc atgtccggga aatctacatg    660
gatnagcaat gagtatgatg gtcaatatgg agaaaaagaa agagtaatta ccaattttt     720
```

-continued

```
ttcaattcaa aaatgtagat gtccgcagcg ttattataaa atgaaagtac attttgataa      780
aacgacaaat tacgatccgt cgtatttata ggcgaaagca ataaacaaat tattctaatt      840
cggaaatctt tatttcgacg tgtctacatt cacgtccaaa tggggccac ttggctgcag       900 ccaagctttc gcgagctcga gatccccgac atatgccccg gtttcgttgc gactaacatg      960
agttcttgga caaatttgat tggacctgat gagatgatcc aacccgagga tatagcaaag     1020
ctcgttcgtg cagcaatgga acggccaaac cgtgcttttg tccccaagaa tgaggtgcta     1080
tgcatgaagg aatctacccg ttgatgtcca acagtctcag ggttaatgtc tatgtatctt     1140
aaataatgtt gtcggtattt tgtaatctca tatagatttt cactgtgcga cgcaaaaata     1200
ttaaataaat attattatta tctacgtttt gattgagata tctagatctc gaggtgtgga     1260
agatatgaat tttttgaga aactagataa gattaatgaa tatcggtgtt ttggtttttt      1320
cttgtggccg tctttgttta tattgagatt tttcaaatca gtgcgcaaga cgtgacgtaa     1380
gtatccgagt cagtttttat ttttctacta atttggtcgt ttatttcggc gtgtaggaca     1440
tggcaaccgg gcctgaattt cgcgggtatt ctgtttctat tccaactttt tcttgatccg     1500
cagccattaa cgacttttga atagatacgt ctagggtcga gggggatcc gtcgaggggg      1560 tccaccaaaa acgtaagcgc ttacgtacat ggtcgagggg gtccaccaaa aacgtaagcg     1620
cttacgtaca tggtcgaggg ggtccaccaa aaacgtaagc gcttacgtac atggtcgagg     1680 ggtccacca aaaacgtaag cgcttacgta catggtcgac tagagcgtga cgctcgcggt      1740
gacgccattt cgccttttca gaaatggata atagccttg cttcctatta tatcttccca      1800
aattaccaat acattacact agcatctgaa tttcataacc aatctcgata caccaaatcg     1860
cggatccgtc gacctgcagg tcgacatgtc tccggagagg agaccagttg agattaggcc     1920
agctacagca gctgatatgg ccgcggtttg tgatatcgtt aaccattaca ttgagacgtc     1980
tacagtgaac tttaggacag agccacaaac accacaagag tggattgatg atctagagag     2040
gttgcaagat agatacccct ggttggttgc tgaggttgag ggtgttgtgg ctggtattgc     2100
ttacgctggg ccctggaagg ctaggaacgc ttacgattgg acagttgaga gtactgttta     2160
cgtgtcacat aggcatcaaa ggttgggcct aggatccaca ttgtacacac atttgcttaa     2220
gtctatggag gcgcaaggtt ttaagtctgt ggttgctgtt ataggccttc caaacgatcc     2280
atctgttagg ttgcatgagg ctttgggata cacagcccgg ggtacattgc gcgcagctgg     2340
atacaagcat ggtggatggc atgatgttgg ttttttggcaa agggattttg agttgccagc     2400
tcctccaagg ccagttaggc cagttaccca gatctgagtc gacggatccc cgacatatgc     2460
cccggtttcg ttgcgactaa catgagttct tggacaaatt tgattggacc tgatgagatg     2520
atccaacccg aggatatagc aaagctcgtt cgtgcagcaa tggaacggcc aaaccgtgct     2580
tttgtcccca gaatgaggt gctatgcatg aaggaatcta cccgttgatg tccaacagtc      2640
tcagggttaa tgtctatgta tcttaaataa tgttgtcggt attttgtaat ctcatataga     2700
ttttcactgt gcgacgcaaa atattaaat aaatattatt attatctacg ttttgattga      2760
gatatcatca atattataat aaaaatatcc attaaacacg atttgataca aatgacagtc     2820
aataatctga tttgaatatt tattaattgt aacgaattac ataaagatcg aatagaaaat     2880
actgcactgc aaatgaaaat taacacatac taataaatgc gtcaaatatc tttgccaaga     2940
tcaagcggag tgagggcctc atatccggtc tcagttacaa gcacggtatc cccgaagcgc     3000
gctccaccaa tgccctcgac atagatgccg ggctcgacgc tgaggacatt gcctaccttg     3060
agcatggtct cagcgccggc tttaagctca atcccatccc aatctgaata tcctatcccg     3120
```

```
cgcccagtcc ggtgtaagaa cgggtctgtc catccacctc tgttgggaat tctgatcttg   3180
gcgcgcatgc ggatcctcat tcctccatca gaagtaactc cacgctatca acaatgaatg   3240
ttccttccgt ttctccaatc tcaatccaaa ccttgtcggt ttctggaaag tactctaact   3300
ctttggtgac atagccggct ggtaacggtg tgtagtcccc atagcctctg ttagattcgc   3360
aaggattgtc cctacgtcca tcggtgtaag ccttctcctc ataggctgat gcatagtcag   3420
cgggtacaga agagttgctc tcataggctc catcgtatcc tcgattgcga gaagtgtaag   3480
taccctcata ctcctcttga gtcgcagtgt agtcattgca agttacggtg ttgtttgggt   3540
agacttcctc ctcgacgcag ttgctgaact tcagctcgtc ggtgttgttc tcaatctcgt   3600
gtatggtgac gcaaccttct ccgtatcctt ctttgtacgc ggtaacacga gaatgtagc    3660 cacgaccagg acagacacga acttcttgtg aaacttctgc ttcccactca ggaacaacaa   3720
ggacagagcg tgattgttc tgttcttcta catctacgtg cccttcaca ttccagcagg     3780 ataggccatt gttgaagtca ccattcttga tgacattcct cgcatcatac aaggagaatg   3840
cagtgaagat gcgcccttct aactcttcaa agatagcagc attgacaccc ggaatcacgc   3900
taagttcagg aaggtaagct tcccgaatgc tatgaacgcg tttgtctgca gcatgaatca   3960
tagctatgtt ggtatcagct tggagcctat catactgaga gttcacaaac agagcgtcaa   4020
cgctttcttt ggcttctttg tacacaatgt ttgtttccca ttccaacttc tctctcttgt   4080
ccctccactt cttctcagcc ctcttcactc tagcgagggc ttctccaaca agtggtttct   4140
cttctagaaa ctccagattg cctagcctgg catggccatc ttgagtcttg atcttgaaga   4200
tcacccacac accgaggtct tcgttcaggt cggtacagcc aacgtctatg tccaaggaga   4260
agtggtgtga gtgatgggca cacttgccga tgggacttgg ggctgaaagt ggccagagtg   4320
aacccgtccc aggcacattg actgtctcat gtttggcgtt gtatctgatg aggtagatct   4380
caaggtcttg actgtcctcg atgtaacctc tcaactggta tcttgtgtag gctttgagtt   4440
tcgattcatc tatcttctgg tacaggtatg ttggatagca ctcatcaaag gtacccaaga   4500
gcgtaacata gttctccttg aacacatcat cacctccttg aatggtgatg tccgtacttc   4560
ccctccatcc acgatctagt tgcctgttga tcccgcgaaa gttgggatct tgaagcaagt   4620
tccgctcatc actaagtcgc ttagcatgtt tgacctttc ggacaactcc ttcttctcat    4680
ccaaacagaa ctcatcagag aggcactcaa caaggttgga aacgcgatcg atgtgatagt   4740
cagtcacatc tgtcttgagc ccaatctgat tggacgaagt gaacagagca ttcaccgcct   4800
tctgtgctct ttccaagtca gactctgcct cgagcgttgc agtaacggga atgaattcga   4860
agcggtcgat tatcactccg gcggttccgg agaaatttct aacacctact atgttaccta   4920
gggaagaggt gaaggcattg gcactttcga agtaaccgaa atcgctagat tggagattat   4980
ccaaggatgt agctgtcgct ggtactgtat tggaaaagat ggaggaatta ccccaattga   5040
cgttgaggtg ataggggta acagaggcat accttacacg aacacgatat ctggtagatg    5100
tcgatgggaa gtgaatgggc acttcaatat accctctatt ctggatgttg ttgccggaag   5160
aattcagcct aaccaagtcg cctccagtga atcctggtcc tgaaatgaca gaaccattaa   5220
agagaaagtt ccccttgaca gctgggatct gagtaatgct atcggatgca attatgttgt   5280
taaactcagc actacgatgt atccaagaga acatcggagc tctgatgata ctaacgctgc   5340
tattactaaa gcctgaacgg aacatggaca catggctaag gcgatggcta aacccttgcc   5400
taggtggaac gttgttgttc tgtggaggga tctcatccaa gctatcaact gttccgctct   5460
```

```
ttctgtagac agcggatggc agatttgagg aggttccata ggcaaattct gtcccgtcaa   5520
gcacagacaa ttgttgattg ttgatgccga tgttgaaagg tctcctatat agagtgctgg   5580
acaaggttct atacacgccc tgaccgagtt gagcaacaat acgttgttgt ggagctgcat   5640
tgcccatagt cccgtaaagt gggaaagtga attctggtcc agagaaccca acgggtgatg   5700
ccatgatctg atgccctgac cagtagtaat aaccgcggtg cgcatcggtg tagatcgtga   5760
tactgttcaa tatgtccatc aggtgtggag acctgatgct tctctctatg ccctgagccg   5820
agcctcgaaa gctaccgtcg aagttctcga ggactgggtt tgtgtagatt tcccgggtca   5880
attgtgacac agtacggatt gggtagcgcc tagagtcgta gttgggaaag agagcgacaa   5940
tgtctaggac agttagtgtc aactctcgcc tgaactggtt gtacctgacc caatctctag   6000
aatccggtcc ccagacacgt tcgagacccg tgttgtacca gcgaacagca taatcggtat   6060
agttgccaat aagcctagtc agatcattat aacgactatt gatagttgcg gcatcaaagc   6120
cccaccgttg tccgaacacg gagacatcgc ggagcaccga caagtgcagg ttggcagcct   6180
gcacgtacac ggataaaaga ggaacttggt aattctgaac ggcgaagagc ggaattgcgg   6240
tcgtcagcgc gctgttcatg tcattgaatt gaatgcgcat ctcctctctt aaggcaggat   6300
tggtcgggtc tgcttcccac tctcgaaaag attctgcgta aatctggtaa aggttgctga   6360
ggccttctaa ccttgagatg gcttggttcc tagcgaattc ttctattctt tggttaatta   6420
actgctctat ctgtacaaga aaggcgtccc attgagaggg accaaagatt ccccaaatga   6480
tatcgacaag tccaagcacg aatccagcac cgggcacgaa ctctgacaaa aggaattggg   6540
taagtgacaa cgagatgtcg ataggtgtgt aaccagtctc aatccgttct ccacccagca   6600
cctcaacctc agggttgctc aggcagttgt aaggaatgca ctcgttgatg ttgggattgt   6660
tgtccattgt tggatcctct agagtcgacc tgcagaagta acaccaaaca acagggtgag   6720
catcgacaaa agaaacagta ccaagcaaat aaatagcgta tgaaggcagg gctaaaaaaa   6780
tccacatata gctgctgcat atgccatcat ccaagtatat caagatcaaa ataattataa   6840
aacatacttg tttattataa tagataggta ctcaaggtta gagcatatga atagatgctg   6900
catatgccat catgtatatg catcagtaaa acccacatca acatgtatac ctatcctaga   6960
tcgatatttc catccatctt aaactcgtaa ctatgaagat gtatgacaca cacatacagt   7020
tccaaaatta ataaatacac caggtagttt gaaacagtat tctactccga tctagaacga   7080
atgaacgacc gcccaaccac accacatcat cacaaccaag cgaacaaaaa gcatctctgt   7140
atatgcatca gtaaaacccg catcaacatg tatacctatc ctagatcgat atttccatcc   7200
atcatcttca attcgtaact atgaatatgt atggcacaca catacagatc caaaattaat   7260
aaatccacca ggtagtttga aacagaattc tactccgatc tagaacgacc gcccaaccag   7320
accacatcat cacaaccaag acaaaaaaaa gcatgaaaag atgacccgac aaacaagtgc   7380
acggcatata ttgaaataaa ggaaaagggc aaaccaaacc ctatgcaacg aaacaaaaaa   7440
aatcatgaaa tcgatcccgt ctgcggaacg gctagagcca tcccaggatt ccccaaagag   7500
aaacactggc aagttagcaa tcagaacgtg tctgacgtac aggtcgcatc cgtgtacgaa   7560
cgctagcagc acggatctaa cacaaacacg gatctaacac aaacatgaac agaagtagaa   7620 ctaccggggcc ctaaccatgg accggaacgc cgatctagag aaggtagaga ggggggggg   7680 gggaggacga gcggcgtacc ttgaagcgga ggtgccgacg ggtggatttg ggggagatct   7740
ggttgtgtgt gtgtgcgctc cgaacaacac gaggttgggg aaagagggtg tggaggggt    7800 gtctatttat tacggcgggc gaggaaggga aagcgaagga gcggtgggaa aggaatcccc   7860
```

-continued

```
cgtagctgcc ggtgccgtga gaggaggagg aggccgcctg ccgtgccggc tcacgtctgc      7920
cgctccgcca cgcaatttct ggatgccgac agcggagcaa gtccaacggt ggagcggaac      7980
tctcgagagg ggtccagagg cagcgacaga gatgccgtgc cgtctgcttc gcttggcccg      8040
acgcgacgct gctggttcgc tggttggtgt ccgttagact cgtcgacggc gtttaacagg      8100
ctggcattat ctactcgaaa caagaaaaat gtttccttag ttttttttaat ttcttaaagg      8160 gtatttgttt aattttttagt cactttattt tattctattt tatatctaaa ttattaaata      8220
aaaaaactaa aatagagttt tagttttctt aatttagagg ctaaaataga ataaaataga      8280
tgtactaaaa aaattagtct ataaaaacca ttaaccctaa accctaaatg gatgtactaa      8340
taaaatggat gaagtattat ataggtgaag ctatttgcaa aaaaaaagga gaacacatgc      8400
acactaaaaa gataaaactg tagagtcctg ttgtcaaaat actcaattgt cctttagacc      8460
atgtctaact gttcatttat atgattctct aaaacactga tattattgta gtactataga      8520
ttatattatt cgtagagtaa agtttaaata tatgtataaa gatagataaa ctgcacttca      8580
aacaagtgtg acaaaaaaaa tatgtggtaa tttttttataa cttcgacatg caatgctcat      8640
tatctctaga gaggggcacg accgggtcac gctgcactgc aggcatgcgc gccttaatta      8700
aggaattcct cgagtttaaa cggatccctg aaagcgacgt tggatgttaa catctacaaa      8760
ttgccttttc ttatcgacca tgtacgtaag cgcttacgtt tttggtggac ccttgaggaa      8820
actggtagct gttgtgggcc tgtggtctca agatggatca ttaatttcca ccttcaccta      8880
cgatgggggg catcgcaccg gtgagtaata ttgtacggct aagagcgaat ttggcctgta      8940
gacctcaatt gcgagctttc taatttcaaa ctattcgggc ctaacttttg gtgtgatgat      9000
gctgactgaa taattacacg gccttcttgt gagacctcgc caatctgctc ggtgtaccct      9060
agcatctcca tatcctcatg tagaagattc aaggaagttg ccttgcatt cagtaccgca       9120 agaccattga acatgttgaa tagatttaca ggttcatcag ccacgctagt gcactcagat      9180
ctggccttcc ggcagtaaga aggatcccag ttccgcctat gcaacattaa aacaaaccta      9240
ggatctccga cctgcagctg agaatatttg gctggtcggg ggactttaaa actcacgata      9300
tgaagatcac aaggtaaggg agtagttaat ggagaaaagg gcccccagtg tgtctgcaca      9360
ttaatgtctt gtggcttctt ggcaatgaat gtgtgtaagg gatgattcaa gtgagcacca      9420
acacaatgcg agagaagaga tggattcaga ggctgtgggt cagaaacggg atttgaagtc      9480
gaagaaatgt tggattcgat caagatatgg aaaacaacat tcataacacg attgtccacc      9540
acaccttgtc caagaccacg accatcgtct tttgccaaac gacggtcaag cataatctct      9600 agccaccccct gtttacagct tgctgcaccc agtgactgcc gagaatggac agaataccta      9660
tggccattgg acccctgcat gaaagcgaga gaaggcatgg ggtagtaatt cccctgcaac      9720
ggaatcttat gatatgtttc tctccgactc atctgaaagc cattcaagtc ggtgtagaaa      9780
attcttttgt tgtcaatatc tgtcttatat ctaacaatta attctttgtc aataaaactg      9840
ttgccgagaa gctcaacatg atattccttc tcaatcagaa actcctggat cgtatttcct      9900
ccattataaa tacgagtact atgggagatc ggagtattct cccatgcagt cttcggataa      9960
gagtacacct cctgcatcaa gggaccctca gagataacca gatgcccacc agattggactt    10020 ataggcacag cttcaccatg gggaacaaat aagtatgcac ctccggtact tgagtaaagg     10080
cttatctctt cagccacggt attttgcaga ccattttttct ggattacctt ttgtaacaaa    10140
ccatgcttga caccaaaggt gagagtttga tgctgattct caatttcaac cacatctcct     10200
```

-continued

```
tctacttctg agcaatcata cagtgtaggg cactgtattg aactcaaatt tgagaagagc    10260
ttgagttttg ccggtttagc tttttcacat ccgacaaagc cattggcaat ataatatgtc    10320
tgcaaaccca tggcaggaac agaagctt                                       10348

<210> SEQ ID NO 4
<211> LENGTH: 21
<212> TYPE: DNA
<213> ORGANISM: Artificial Sequence
<220> FEATURE:
<223> OTHER INFORMATION: Forward primer 281-14

<400> SEQUENCE: 4
tgtcggctga aggtagggag g                                              21

<210> SEQ ID NO 5
<211> LENGTH: 20
<212> TYPE: DNA
<213> ORGANISM: Artificial Sequence
<220> FEATURE:
<223> OTHER INFORMATION: Reverse primer 281-15

<400> SEQUENCE: 5
ccggacatga agccatttac                                                20

<210> SEQ ID NO 6
<211> LENGTH: 603
<212> TYPE: DNA
<213> ORGANISM: Artificial Sequence
<220> FEATURE:
<223> OTHER INFORMATION: 603 bp sequence of the amplicon produced using
      the primers of SEQ ID NO:4 and SEQ ID NO:5

<400> SEQUENCE: 6
tgtcggctga aggtagggag gaattaatca atcacagttg cttgtttctg agtctataga    60
atcatgaatt ttaaatttat ggaatgcatt ttttcgaaga tattgtatgc attaagtgta    120
attttagttt caatatgaaa tttgagattt atatatatac ttacataaaa ccctccttta    180
ctgaattagt gccatggata aaagaccaat taagcaatcc ttccaacacg tgcatgcact    240
ggattttcat cgcctcgtcc attgttaaat tgataggtta ataagaacaa ttagttggct    300
actgattata tggattctgg gttaaaagta tttaggttta ctgttacata catggaggat    360
ctacatctat tttcactttt gtttaattaa tttaagttag ttttgatgag tttaaggatt    420
gtactagcca atagtagtac ataaaggaga tagagtacca aaacaaagaa aaagccgaaa    480
ggtgttaatg ctaaattgta aaagaaagtt aaaataagag actcgaatta taatatgatt    540
ctctggcgca ctaattaagc tactatatat tgtcaatagt attgtaaatg gcttcatgtc    600
cgg                                                                  603

<210> SEQ ID NO 7
<211> LENGTH: 21
<212> TYPE: DNA
<213> ORGANISM: Artificial Sequence
<220> FEATURE:
<223> OTHER INFORMATION: Forward primer 281-9

<400> SEQUENCE: 7
tctctagaga ggggcacgac c                                              21

<210> SEQ ID NO 8
<211> LENGTH: 21
<212> TYPE: DNA
```

<213> ORGANISM: Artificial Sequence
<220> FEATURE:
<223> OTHER INFORMATION: Reverse primer 281-10

<400> SEQUENCE: 8
cgagctggag agaccggtga c							21

<210> SEQ ID NO 9
<211> LENGTH: 562
<212> TYPE: DNA
<213> ORGANISM: Artificial Sequence
<220> FEATURE:
<223> OTHER INFORMATION: 562 bp sequence of the amplicon produced using
      the primers of SEQ ID NO:7 and SEQ ID NO:8

<400> SEQUENCE: 9
tctctagaga ggggcacgac cgggtcacgc tgcactgcag ccaagtggcc cccatttgga			60 cgtgaatgta gacacgtcga aataaagatt tccgaattag ataaatttgc ttattgcttt			120 cgcctataaa tacgacggat cgtaatttgt cgctttatca gaatgtactt tcattttata			180 ataacgctgc ggacatctac atttttgaat tgaaaaaaaa ttggtaatta ctctttcttt			240 ttctccatat tgaccatcat actcattgct gatccatgta gatttccctt acttgtctcc			300 ctctaatctg actttattaa cccaaagcaa ttgcttattt gttccccacg cccacaaagc			360 ccagcattgt ccctaaggta ttaatttgtt gttcgattct tgttcttgaa cccatttgga			420 gaatgcaaca agggttttca tgtcagcacg gtaatggttc tgtgtaaatt ccagtagtgc			480 tgcccaagta aagtctgggt atttcctcga atttgcggca ttaactaagc tagctgctgg			540 tgtcaccggt ctctccagct cg							562

<210> SEQ ID NO 10
<211> LENGTH: 25
<212> TYPE: DNA
<213> ORGANISM: Artificial Sequence
<220> FEATURE:
<223> OTHER INFORMATION: Forward primer 3006-20

<400> SEQUENCE: 10
ttccaacctt taactattat cctgc							25

<210> SEQ ID NO 11
<211> LENGTH: 20
<212> TYPE: DNA
<213> ORGANISM: Artificial Sequence
<220> FEATURE:
<223> OTHER INFORMATION: Reverse primer 3006-22

<400> SEQUENCE: 11
gctgcggaca tctacatttt							20

<210> SEQ ID NO 12
<211> LENGTH: 614
<212> TYPE: DNA
<213> ORGANISM: Artificial Sequence
<220> FEATURE:
<223> OTHER INFORMATION: 614 bp sequence of the amplicon produced using
      the primers of SEQ ID NO:10 and SEQ ID NO:11

<400> SEQUENCE: 12
ttccaacctt taactattat cctgccttaa aattcgaata catttattat ctataaacta			60 tccgaatatt attatctaaa tcctaattaa atactatttt ttatcgagta ttcgtatccg			120 ccaaggaaat ccatctccaa attttcaatt atttttcaga tatctaaatc tgtaaaattt			180

```
caaattcaag tacgttacaa ttctttataa ataatccaaa ttataaatat tttataacta    240
ttaattcata aattaaaatt tattattcaa atattcgaat aatctatttt taagacgtaa    300
agtattacat cgaagggtta ctttcaaagg gtagtgtatt tccatttcaa ttattcagaa    360
cgttgtcgtt ttgttccggt catagaaaag ggctctggaa gagaagaaaa tgacttgact    420
tttcaatttc atgctcatcc actcgtttca attactgttt actaaaaaaa taataaaata    480
aaatattaac aatgcattga gtatgatgtc cgggaaatct acatggatca gcaatgagta    540
tgatggtcaa tatggagaaa aagaaagagt aattaccaat tttttttcaa ttcaaaaatg    600
tagatgtccg cagc                                                     614

<210> SEQ ID NO 13
<211> LENGTH: 24
<212> TYPE: DNA
<213> ORGANISM: Artificial Sequence
<220> FEATURE:
<223> OTHER INFORMATION: Forward primer 3006-9

<400> SEQUENCE: 13
gacatgcaat gctcattatc tcta                                          24

<210> SEQ ID NO 14
<211> LENGTH: 22
<212> TYPE: DNA
<213> ORGANISM: Artificial Sequence
<220> FEATURE:
<223> OTHER INFORMATION: Reverse primer 3600-12

<400> SEQUENCE: 14
aagtctctgc cttctaccct gg                                            22

<210> SEQ ID NO 15
<211> LENGTH: 662
<212> TYPE: DNA
<213> ORGANISM: Artificial Sequence
<220> FEATURE:
<223> OTHER INFORMATION: 662 bp sequence of the amplicon produced using
      the primers of SEQ ID NO:13 and SEQ ID NO:14

<400> SEQUENCE: 15
gacatgcaat gctcattatc tctagagagg ggcacgaccg ggtcacgctg cactgcaggc    60
atgcgcgcct taattaagga attcctcgag tttaaacgga tccctgaaag cgacgttgga    120
tgttaacatc tacaaattgc cttttcttat cgaccatgta cgtaagcgct tacgtttttg    180
gtggacccct gaggaaactg gtagctgttg tgggcctgtg gtctcaagat ggatcattaa    240
tttccacctt cacctacgat gggggcatc gcaccggtga gtaatattgt acggctaaga    300
gcgaatttgg cctgtagacc tcaattgcga gctttctaat ttcaaactat tcgggcctaa    360
cttttggtgt gatgatgctg actggcttac gtgtggaaaa aatttgcaat ctatgtagtc    420
tttaactaat gttttttct taaaaaaaa agtcattatt tttggtttga ttaatatatt    480
tggtttaaat taaataaaat attaaaaagt ttagttaaat catctatta aacgatttgt    540 actgatttgt gatctattaa ttttttaact taatctagac cagggtacta gttggtccga    600
tcccatcttg aaaacactat ctttagcttg ctggtaggtt ccagggtaga aggcagagac    660
tt                                                                  662

<210> SEQ ID NO 16
<211> LENGTH: 20
```

```
<212> TYPE: DNA
<213> ORGANISM: Artificial Sequence
<220> FEATURE:
<223> OTHER INFORMATION: Forward primer 3006-23

<400> SEQUENCE: 16
gaatcaatct tttacgggaa                                                20

<210> SEQ ID NO 17
<211> LENGTH: 20
<212> TYPE: DNA
<213> ORGANISM: Artificial Sequence
<220> FEATURE:
<223> OTHER INFORMATION: Reverse primer 3006-25

<400> SEQUENCE: 17
catgtagatt tcccggacat                                                20

<210> SEQ ID NO 18
<211> LENGTH: 660
<212> TYPE: DNA
<213> ORGANISM: Artificial Sequence
<220> FEATURE:
<223> OTHER INFORMATION: 660 bp sequence of the amplicon produced using
      the primers of SEQ ID NO:16 and SEQ ID NO:17

<400> SEQUENCE: 18
gaatcaatct tttacgggaa aactcaattg gaatgaaact tgtttccagt aaaagtatta    60
aaaaatgtat aaactagtcc atgtatgata gtgtaaagag tatattggag ttaaaaattt   120
catcccatgt tactctatat tacattataa aggaagctat aggttggctc actgcaccac   180
ccaatcaaga tactcatatg tattacttaa tatataatat taaagatat catttctttt    240 tgttatcaga ttaaagagaa ctaagatatt acaaacttgc aaaacaatag ttaggccaac   300
ccatatttta aatattttct tcttttttct actcaaacct attttgtttc caaatattga   360
agagttctgt tctgattgga tatactctcg gacaagttta actctaaatt ttccaaatat   420
tgaaatatgg atttgctcac atggaaaaac ggttcttgaa caataaatca aaatagcata   480
ttctatcaat ggaatcaagg aattccatat tcatttcaaa gttggagcca agcatgcatg   540
ataatgattt atagcaattt tgtcaaaagg aaaaaataag gtgattggat gacaagaaac   600
aaagggaaaa tgaattaaca gcctgcattt aatatcattc atgtccggga atctacatg    660

<210> SEQ ID NO 19
<211> LENGTH: 24
<212> TYPE: DNA
<213> ORGANISM: Artificial Sequence
<220> FEATURE:
<223> OTHER INFORMATION: Forward primer 3006-9

<400> SEQUENCE: 19
gacatgcaat gctcattatc tcta                                           24

<210> SEQ ID NO 20
<211> LENGTH: 24
<212> TYPE: DNA
<213> ORGANISM: Artificial Sequence
<220> FEATURE:
<223> OTHER INFORMATION: Reverse primer 3006-11C

<400> SEQUENCE: 20
gaacctgtaa atctattcaa catg                                           24
```

-continued

```
<210> SEQ ID NO 21
<211> LENGTH: 531
<212> TYPE: DNA
<213> ORGANISM: Artificial Sequence
<220> FEATURE:
<223> OTHER INFORMATION: 531 bp sequence of the amplicon produced using
      the primers of SEQ ID NO:19 and SEQ ID NO:20

<400> SEQUENCE: 21
gacatgcaat gctcattatc tctagagagg ggcacgaccg ggtcacgctg cactgcaggc      60
atgcgcgcct taattaagga attcctcgag tttaaacgga tccctgaaag cgacgttgga     120
tgttaacatc tacaaattgc cttttcttat cgaccatgta cgtaagcgct tacgtttttg     180
gtggaccctt gaggaaactg gtagctgttg tgggcctgtg gtctcaagat ggatcattaa     240 tttccaccttt cacctacgat gggggcatc gcaccggtga gtaatattgt acggctaaga    300
gcgaatttgg cctgtagacc tcaattgcga gctttctaat ttcaaactat tcgggcctaa    360
cttttggtgt gatgatgctg actgaataat tacacggcct tcttgtgaga cctcgccaat    420
ctgctcggtg taccctagca tctccatatc ctcatgtaga agattcaagg aagttggcct    480
tgcattcagt accgcaagac cattgaacat gttgaataga tttacaggtt c             531
```